United States Patent [19]

Guthikonda et al.

[11] Patent Number: 5,128,335
[45] Date of Patent: Jul. 7, 1992

[54] 2-HETEROARYLPHENYL-CARBAPENEM ANTIBACTERIAL AGENTS

[75] Inventors: Ravindra N. Guthikonda, Edison; Susan M. Schmitt, South Plains; Frank P. Dininno, Old Bridge, all of N.J.

[73] Assignee: Merck & Co., Inc., Rahway, N.J.

[21] Appl. No.: 597,638

[22] Filed: Oct. 15, 1990

[51] Int. Cl.$^5$ .................. C07D 487/04; A61K 31/40
[52] U.S. Cl. ..................................... 514/210; 540/302
[58] Field of Search .......................... 540/302; 514/210

[56]         References Cited
         U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Christensen et al. | 514/210 |
| 4,775,669 | 10/1988 | Cama et al. | 514/210 |

FOREIGN PATENT DOCUMENTS 027743  8/1988  European Pat. Off. .

OTHER PUBLICATIONS

L. D. Cama et al., Total Synthesis of Thienamycin Analogs-III, Tetrahedron 39, 2531 (1983).
R. N. Guthikonda, et al., Structure Activity Relationships in the 2-Arylcarbapenem Series, *J. Med. Chem.*, 30, 871 (1987).

*Primary Examiner*—Mukund J. Shah
*Assistant Examiner*—Jyothsna Venkat
*Attorney, Agent, or Firm*—Gabriel Lopez; Joseph F. DiPrima

[57]           ABSTRACT

Carbapenems of the formula

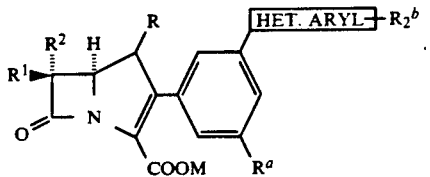

are useful antibacterial agents.

12 Claims, No Drawings

2-HETEROARYLPHENYL-CARBAPENEM ANTIBACTERIAL AGENTS

BACKGROUND OF THE INVENTION

The present invention relates to antibacterial agents of the carbapenem class, in which the 2-position sidechain is characterized by a heteroarylphenyl moiety, substituted by various substituents, as described in more detail below.

Thienamycin was an early carbapenem antibacterial agent having a broad spectrum; it has the following formula:

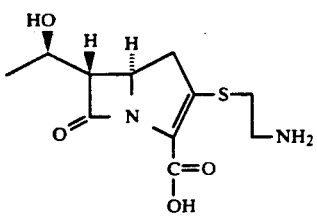

Later, N-formimidoyl thienamycin was discovered; it has the formula:

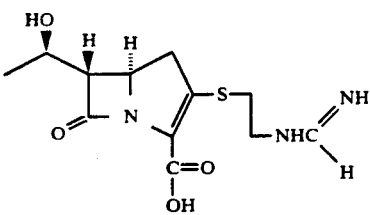

The 2-heteroarylphenyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

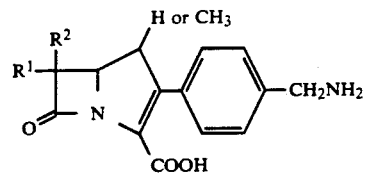

However, there is no description or suggestion of a heteroarylphenyl 2-substituent such as characterizes the compounds of the present invention, nor is there any suggestion of the suprisingly better anti-MRSA/MRCNS activity of the compounds of the present invention.

EP-A-0277 743 describes a particular class of compounds of the formula:

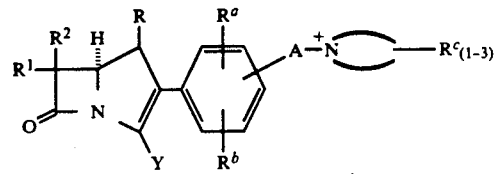

but this limited teaching is no way suggests the totally different compounds of the present invention, nor their surprisingly better anti-MRSA/MRCNS activity.

SUMMARY OF INVENTION

The present invention provides novel carbapenem compounds of the formula:

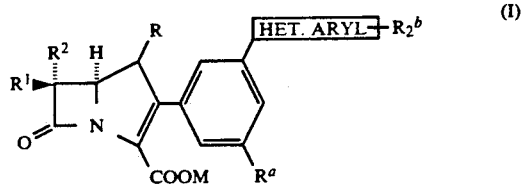

wherein:

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

|HET. ARYL| is (a) a monocyclic 5- or 6-membered aromatic ring system wherein at least one carbon atom is replaced by N, up to four additional carbon atoms may be replaced by N, and one carbon atom may be replaced by O or S; or (b) a bicyclic 9- or 10-membered aromatic ring system wherein at least one carbon atom is replaced by N, up to three additional carbon atoms may be replaced by N, and up to two carbon atoms may be replaced by S and/or O; with the proviso for both (a) and (b) that the atom in

|HET. ARYL| at the point of attachment to the phenyl-$R^a$ ring is always carbon;

may be quaternized to form a cationic ring structure:

[HET. ARYL]—$R_d^+$ wherein $R_d$ is $NH_2$, $O^-$, or $C_1$-$C_4$ alkyl (where the alkyl group is optionally monosubstituted with $R^q$ as defined below); $R^a$ and $R^b$ are independently selected from the group consisting of hydrogen and the radicals set out below:

a) a trifluoromethyl group: $-CF_3$;
b) a halogen atom: $-Br$, $-Cl$, $-F$, or $-I$;
c) $C_1$-$C_4$ alkoxy radical: $-OC_1$-$C_4$ alkyl, wherein the alkyl is optionally mono-substituted by $R^q$, where $R^q$ is a member selected from the group consisting of $-OH$, $-OCH_3$, $-CN$, $-C(O)NH_2$, $-OC(O)NH_2$, $CHO$, $-OC(O)N(CH_3)_2$, $-SO_2NH_2$, $-SO_2N(CH_3)_2$, $-SOCH_3$, $-SO_2CH_3$, $-F$, $-CF_3$, $-COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and $-SO_3M^b$ (where $M^b$ is hydrogen or an alkali metal);
d) a hydroxy group: $-OH$;
e) a carbonyloxy radical: $-O(C=O)R^s$, where $R^s$ is $C_{1-4}$ alkyl or phenyl, each of which is optionally mono-substituted by $R^q$ as defined above;
f) a carbamoyloxy radical: $-O(C=O)N(R^y)R^z$, where $R^y$ and $R^z$ are independently H, $C_1$-$C_4$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by $-O-$, $-S-$, $-S(O)-$, $-S(O)_2-$ or $-NR^e-$, to form a ring (where $R^e$ is hydrogen, $C_1$-$C_4$ alkyl, and $C_1$-$C_4$ alkyl mono-substituted with $R^q$ and the ring is optionally mono-substituted with $R_q$ as defined above);
g) a sulfur radical: $-S(O)_n-R^s$ where $n=0-2$, and $R^s$ is defined above;
h) a sulfamoyl group: $-SO_2N(R^y)R^z$ where $R^y$ and $R^z$ are as defined above;
i) azido: $N_3$
j) a formamido group: $-N(R^f)-C(O)H$, where $R^f$ is H or $C_1$-$C_4$ alkyl, and the alkyl thereof is optionally mono-substituted by $R^q$ as defined above;
k) a $(C_1$-$C_4$ alkyl)carbonylamino radical: $-N(R^f)-C(O)C_1$-$C_4$ alkyl, where $R^f$ is as defined above, and the alkyl group is also optionally mono-substituted by $R^q$ as defined above;
l) a $(C_1$-$C_4$ alkoxy) carbonylamino radical: $-N(R^f)-C(O)OC_{1-4}$ alkyl, where $R^f$ is as defined above, and the alkyl group is also optionally mono-substituted by $R^q$ as defined above;
m) a ureido group: $-N(R^f)-C(O)N(R^y)R^z$ where $R^f$, $R^y$ and $R^z$ are as defined above;
n) a sulfonamido group: $-N(R^f)SO_2R^s$, where $R^s$ and $R^f$ are as defined above;
o) a cyano group: $-CN$;
p) a formyl or acetalized formyl radical: $-C(O)H$ or $-C(OCH_3)_2H$;
q) $(C_1$-$C_4$ alkyl)carbonyl radical wherein the carbonyl is acetalized: $-C(OCH_3)_2C_1$-$C_4$ alkyl, where the alkyl is optionally mono-substituted by $R^q$ as defined above;
r) carbonyl radical: $-C(O)R^s$, where $R^s$ is as defined above;
s) a hydroximinomethyl radical in which the oxygen or carbon atom is optionally substituted by a $C_1$-$C_4$ alkyl group: $-C(R^y)=NOR^z$ where $R^y$ and $R^z$ are as defined above, except they may not be joined together to form a ring;
t) a $(C_1$-$C_4$ alkoxy)carbonyl radical: $-C(O)OC_1$-$C_4$ alkyl, where the alkyl is optionally mono-substituted by $R^q$ as defined above;
u) a carbamoyl radical: $-C(O)N(R^y)R^z$ where $R^y$ and $R^z$ are as defined above;
v) an N-hydroxycarbamoyl or $N(C_1$-$C_4$ alkoxy)carbamoyl radical in which the nitrogen atom may be additionally substituted by a $C_1$-$C_4$ alkyl group: $-(C=O)-N(OR^y)R^z$ where $R^y$ and $R^z$ are as defined above, except they may not be joined together to form a ring;
w) a thiocarbamoyl group: $-C(S)N(R^y)(R^z)$ where $R^y$ and $R^z$ are as defined above;
x) carboxyl: $-COOM^b$, where $M^b$ is as defined above;
y) thiocyanate: $-SCN$;
z) trifluoromethylthio: $-SCF_3$;
aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;
ab) an anionic function selected from the group consisting of: phosphono $[P=O(OM^b)_2]$; alkylphosphono $\{P=O(OM^b)-[O(C_1$-$C_4$ alkyl$)]\}$; alkylphosphinyl $[P=O(OM^b)-(C_1$-$C_4$ alkyl$)]\}$; phosphoramido $[P=O(OM^b)N(R^y)R^z$ and $P=O-(OM^b)NHR^x]$; sulfino $(SO_2M^b)$; sulfo $(SO_3M^b)$; acylsulfonamides selected from the structures $CONM^bSO_2R^x$, $CONM^bSO_2N(R^y)R^z$, $SO_2NM^bCON(R^y)R^z$; and $SO_2NM^bCN$, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;
ac) $C_2$-$C_4$ alkenyl radical, optionally mono-substituted by one of the substituents a) to ab) above and phenyl which is optionally substituted by $R^q$ as defined above;
ad) $C_2$-$C_4$ alkynyl radical, optionally mono-substituted by one of the substituents a) to ab) above;
ae) $C_1$-$C_4$ alkyl radical;
af) $C_1$-$C_4$ alkyl mono-substituted by one of the substituents a)-ab) above;
ag) an amino group, $NR^f_2$, wherein $R^f$ is as defined above;

M is selected from:

i) hydrogen;
ii) a pharmaceutically acceptable esterifying group or removable carboxyl protecting group;
iii) an alkali metal or other pharmaceutically acceptable cation; or
iv) a negative charge which is balanced by a positively charged group.

DETAILED DESCRIPTION OF THE INVENTION

The manufacture of compounds of Formula I may be carried out in a three-stage synthetic scheme followed by deprotection. The objective of the first synthetic stage is to produce a base heteroarylphenyl (hereinafter HAP) compound which may be converted to be the two-position substituent of the carbapenem of Formula I. The objective of the second synthetic stage is to attach the base HAP to the carbapenem. Finally, the objective of the third synthetic stage is to substitute the HAP with the desired $R^a$ and $R^b$. This third synthetic stage may either be performed after the first synthetic stage or after the second synthetic stage according to the nature of the desired $R^a$ and $R^b$.

Flow Sheet A demonstrates a suggested first synthetic stage. Flow Sheet B demonstrates a second synthetic stage. The third synthetic stage varies according to the selected $R^a$ and $R^b$.

FLOW SHEET A

Substituted bromophenylboronic acids A1 and substituted heteroaryldiethylboranes A5 may be prepared by conventional methods. Exposure of either of these boron compounds to aryl halides such as A2 or A4 in the presence of a catalytic amount of palladium catalyst yields the desired synthons A3.

FLOW SHEET A

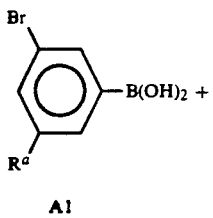

A1

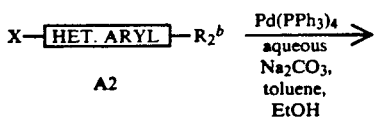

A2

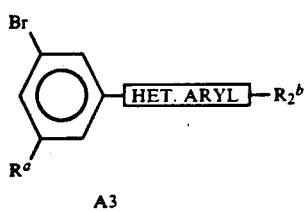

A3

Alternatively,

-continued
FLOW SHEET A

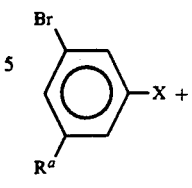

A1

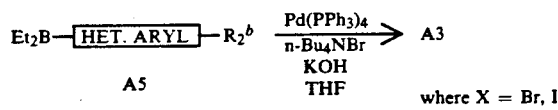

A5 where X = Br, I

FLOW SHEET B

The second synthetic stage is to attach the base HAP to the 2-position of the carbapenem. With compatible $R^a$ or $R^b$ or suitable precursor substituents therefor, HAP A3 may be added to azetidin-2-one B1 in a Grignard reaction as shown in Flow Sheet B. (B1 is subgeneric to the more general B1*. Replacing B1 by B1* (where M is as defined above under ii) produces a broader class of compounds analogous to B2, B3 and B4).

The Grignard reaction requires that A3 be converted to a Grignard reagent by reaction with magnesium and 1,2-dibromoethane in THF from 20° C. to 60° C. and subsequently contacting A3 as a Grignard reagent with B1 in THF at from −70° C. to about 20° C. to produce azetidin-2-one B2. Alternatively, A3 may be reacted with t-butyllithium, n-butyllithium, or the like in Et$_2$O or THF at from −78° to −50° C. followed by the addition of magnesium bromide to produce the same Grignard reagent. $R^i$ of B1 is in practice pyrid-2-yl but may clearly be a variety of substituents including aromatic and heteroaromatic substituents. Further $R^i$ might be for example phenyl, pyrimidinyl or thiazolyl.

Azetidin-2-one B2 is an intermediate that may be ring closed to a carbapenem. It is on this intermediate that $R^a$ or precursor substituent such as t-butyldimethylsilyloxy-methyl group should be modified where such modification is incompatible with the carbapenem nucleus. For example, a convenient reaction to remove the t-butyldimethylsilyl group from a hydroxymethyl substituent of the HAP on compound B2 is to expose compound B2 to a dilute solution of sulfuric acid in methanol at 0° C. If the t-butyldimethylsilyl group were removed from carbapenem B3 under the same conditions, a substantial portion of carbapenem would be degraded and lost. Thus, modification of the precursor substituent in this instance and replacement with another precursor substituent or even $R^a$ is best performed before closing the carbapenem. Of course it is possible to remove the t-butyldimethylsilyl group from carbapenem B3 in reduced yield by exposing B3 to tetra-n-butylammonium fluoride and acetic acid in THF.

Compound B2 may be ring closed to carbapenem B3 by refluxing in xylene with p-hydroquinone for about 1 to 2 hours. It is on this intermediate that final elaboration of $R^a$ from a precursor substituent, e.g. hydroxymethyl, may be accomplished. Removal of the protecting groups then provides the final compound Formula I. Such final elaboration and deprotection is described in further detail below.

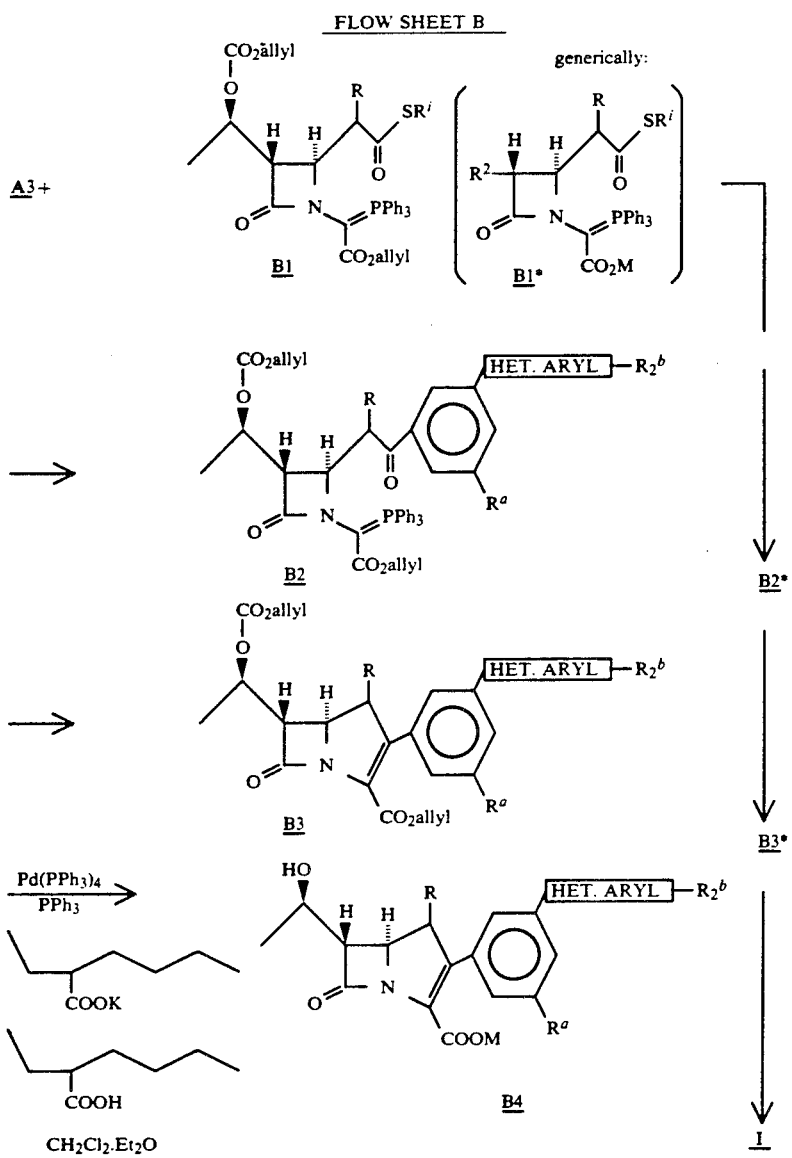

FLOW SHEET C

Azetidin-2-ones B1 and B1*, pyridyl-thioesters, are well known compounds in the production of carbapenems. Diverse synthetic schemes useful to make B1 and B1* may be imagined by the skilled artisan. Particularly useful to the instant inventors is a synthetic scheme set out further in Flow Sheet C below in which the symbol R is as defined above. The steps for preparing intermediate B1 and B1* are analogous to the procedures described, for example, in U.S. Pat. Nos. 4,260,627 and 4,543,257; L. D. Cama et al. *Tetrahedron*, 39, 2531 (1983); R. N. Guthikonda et al. *J. Med. Chem.*, 30, 871 (1987) hereby incorporated by reference and as discussed below.

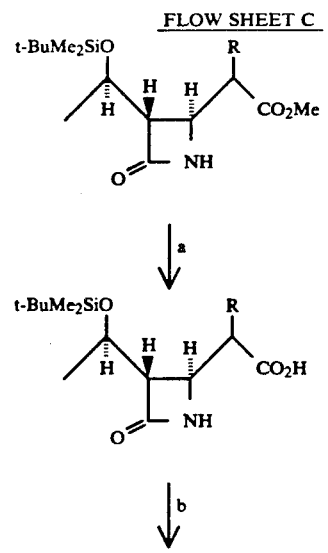

-continued
FLOW SHEET C

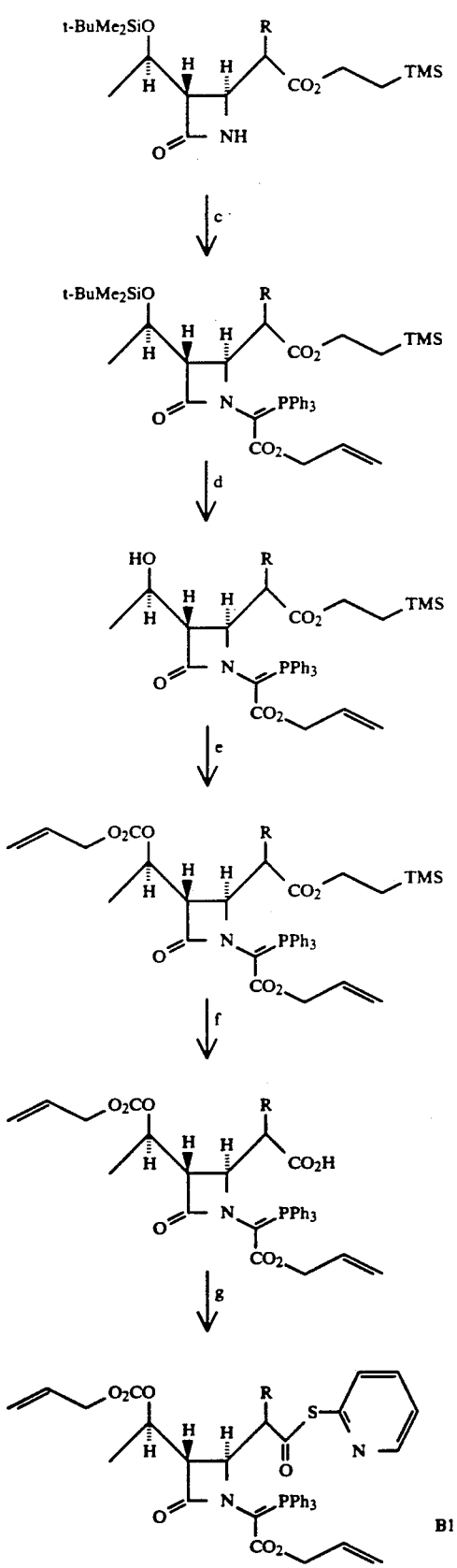

-continued
FLOW SHEET C a. NaOH/MeOH
b. carbonyl diimidazole/HO~~~TMS
c. i. OHCCO₂~~~
d. 6NHClMeOH
e. ClCO₂P~~~/DMAP
f. nBu₄NF
g. Pyr-SS-Pyr./Ph₃P The general synthetic description depicted above in the Flow Sheets shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanruku Ocean).

In the compounds of the present invention, the $R^a$ and $R^b$ substituents can be selected based on the biological properties which they confer. In related compounds, it has been found that the neutral or anionic substituted compounds afford greater water solubility and reduced potential for CNS side effects. Substituents which tend to confer improved water solubility on the overall compound have been found useful, since they are contemplated to thereby improve the transport of the compound involved. Although a substantial number and range of substituents have been described herein, all of these are contemplated to be a part of the present invention based on the biological performance of substituents related in terms of their medicinal chemistry.

HET. ARYL is (a) a monocyclic 5- or 6-membered aromatic ring system wherein at least one carbon atom is replaced by N, up to four additional carbon atoms may be replaced by N, and one carbon atom may be replaced by O or S; or (b) a bicyclic 9- or 10-membered aromatic ring system wherein at least one carbon atom is replaced by N, up to three additional carbon atoms may be replaced by N, and up to two carbon atoms may be replaced by S and/or O; with the proviso for both (a) and (b) that the atom in

HET. ARYL at the point of attachment to the phenyl-$R^a$ ring is always carbon. Thus, this aryl structure may be the radical of a 5-membered oxatriazole, thiatriazole, tetrazole, oxadiazole, thiadiazole, triazole, isoxazole, oxazole, isothiazole, thiazole, pyrazole, imidazole, or pyrrole; of a 6-membered tetrazine, triazine, diazine, or pyridine; or of a 9- or 10-membered quinoline, isoquinoline, etc. The carbon atom at the point of attachment cannot be replaced by a heteroatom; and in the case of pyridine, the attachment is to the 3-position of the pyridine nucleus.

fonate, or the like, gives the N-aminopyridinium salt D3.

FLOW SHEET D

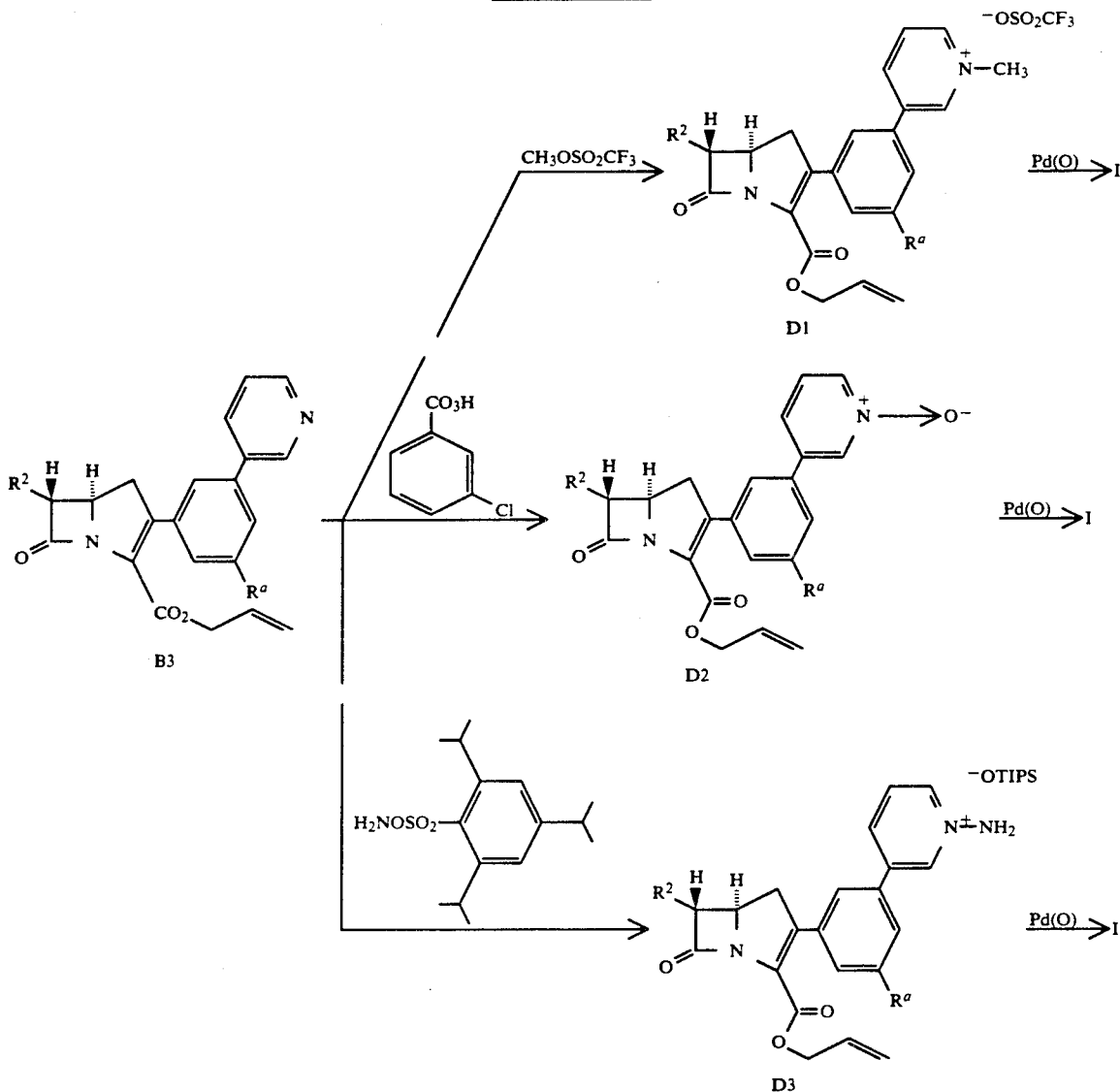

The $R^b$ substituents are on the carbon atoms of the aryl ring but not on the one at the point of attachment.

The nitrogen atom(s) of the heteroaromatic ring may be quarternized to form a cationic ring structure:

wherein $R_d$ is $NH_2$, O—, or $C_1$-$C_4$ alkyl (where the alkyl group is optionally monosubstituted with Rq as defined above). This is exemplified in Flow Sheet D in which a fully elaborated carbapenem B3 is exposed to an alkylating agent such as methyl triflate or the like, to provide a pyridinium salt D1, which in turn can be deprotected to provide the compounds I of the invention. Similarly, oxidation of B3 with m-chloroperbenzoic acid or the like, yields the desired pyridine N-oxide intermediate D2 which can also be analogously processed to I. Lastly, treatment of B3 with an aminating agent, such as O-amino-2,4,6-triisopropylbenzenesul- In preferred compounds of Formula I, $R^1$ is hydrogen. More preferably, $R^1$ is hydrogen and $R^2$ is (R)—CH$_3$CH(OH)— or (R)—CH$_3$CH(F)—. In the most preferred case, $R^1$ is H and $R^2$ is (R)—CH$_3$CH(OH).

While R═H is usually preferred, there are instances in which R═CH$_3$ may provide improved chemical stability, water solubility, or pharmacokinetic behavior. The substituent R═CH$_3$ may be of either configuration, i.e., the α or β-stereoisomer. Additionally, in preferred compounds, $R^b$ is hydrogen when it is adjacent to the point of attachment to the phenyl ring. In the most preferred compounds, $R^a$ is not hydrogen.

Among preferred $R^a$ and $R^b$ substituents are $C_1$-$C_4$ alkyl mono-substituted with hydroxy, such as, hydroxymethyl; formyl; carbamoyl, such as, —CONH$_2$; hydroxyiminomethyl, such as, —CH═NOH; cyano; and halogen such as chloro, bromo and iodo.

Flow Sheet E

In regard to this preferred substitution, the hydroxymethyl group may be obtained in the $R^a$ position of the HAP as shown in Flow Sheet E, in which A3 is obtained as given in Flow Sheet A. Selective metallation of A3 and formylation with dimethylformamide provides synthon E1. Reduction of E1 with sodium borohydride in methanol yields the preferred substituent which is protected as its silylether in the next step to give E3. The latter reagent is then incorporated into Flow Sheet B as A3. The preferred hydroxymethyl group may also be obtained in the appropriate positions of the heteroaryl portion of HAP designated heretofore as $R^b$. Thus, by a judicious choice of starting materials as exhibited in Flow Sheet A, the desired substitution pattern is readily available.

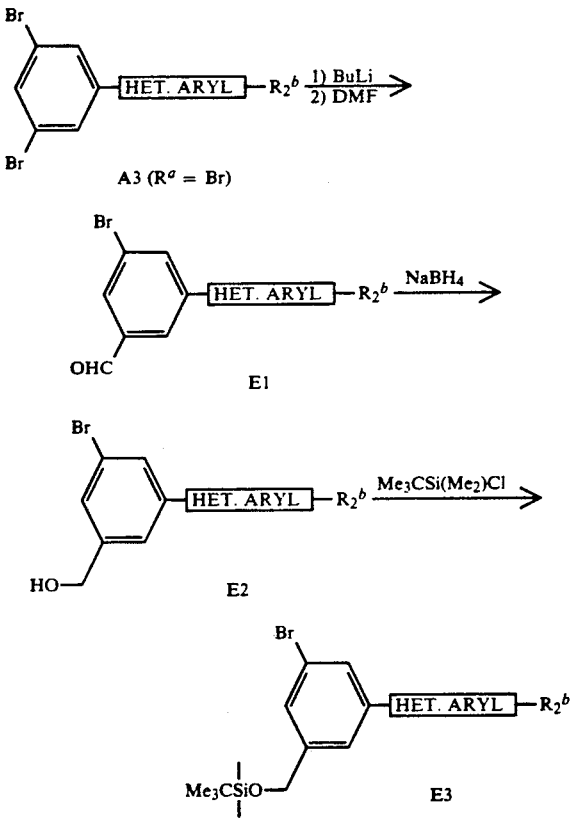

FLOW SHEET E

The preferred formyl substitution on the HAP moiety may be obtained from the hydroxymethyl substitution of B3 or isomeric B3 described in Flow Sheet B by a Swern oxidation. For example, isomeric B3 is oxidized in methylene chloride at from $-70°$ C. to room temperature employing oxalyl chloride-dimethyl sulfoxide as the active agent. Obviously, the position of the resultant formyl substitution will depend upon the position of the hydroxymethyl substitution in isomeric B3.

The preferred —CH=NOH substitution on the HAP moiety may be conveniently obtained from the formyl substitution just described. This is accomplished simply by exposing the formyl substituted compound to hydroxylamine in an appropriate solvent at room temperature.

The preferred cyano substitution on the HAP moiety may be obtained from the —CH=NOH substitution just described. The —CH=NOH substituted compound is dehydrated with triflic anhydride and triethylamine in a solvent at $-70°$ C.

The —COOK substitution on the HAP moiety may be obtained from the hydroxymethyl substituted B2 or isomeric B2 described above. For example, an isomeric B2 is oxidized with Jones reagent to replace the hydroxymethyl group with a carboxylic acid group. The oxidation with Jones reagent may be incompatible with the carbapenem and thus is optionally performed before ring closure. Prior to ring closure, the carboxy group is protected as its allyl ester to permit cyclization of the carbapenem. Protection is carried out by alkylating with allyl bromide and triethylamine. Deprotection following cyclization is carried out with palladium catalyzed deallylation in a solution containing potassium or sodium 2-ethylhexanoate as described in McCombie and Jeffrey, *J. Org. Chem.*, 47, 2505 (1983). Deprotection in such a solution yields the desired potassium or sodium salt.

The preferred carbamoyl substitution, —CONH$_2$, may be obtained from B2 or "isomeric" B2 by oxidizing hydroxymethyl with Jones reagent to the corresponding carboxylic acid substitution as described above. This carboxylic acid is converted to —CONH$_2$ by sequentially contacting with 1-ethyl-3-(3-dimethyl-aminopropyl)carbodiimide hydrochloride, 1-hydroxy-benzotriazole, and ammonia in an organic solvent at room temperature. Substituted amides may of course be obtained by replacing ammonia with the corresponding substituted amine. In contrast to the carboxylic acid substitution, this carbamoyl substituent requires no protection from the conditions of carbapenem cyclization.

In the preparation methods described above, the carboxyl group at the 3-position and the hydroxyl group at the 8-position of the carbapenem remain blocked by protecting groups until the final product is prepared. Deblocking may be carried out in a conventional manner, with care being taken to avoid a procedure which is so harsh as to disrupt other portions of the final product molecule.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1 O or 1S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2N's) and triazine (3N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Table I are specific compounds of the instant invention. In this table, compounds that have an $R^2$ containing a chiral center (e.g., —CH(F)CH$_3$ and —CH(OH)CH$_3$) have the (R) configuration.

TABLE I

(I')

| No. | R | $R^2$ | M | $R^a$ | HET. ARYL—$R^b$ |
|---|---|---|---|---|---|
| 1 | H | —CH(OH)CH$_3$ | Na | H | 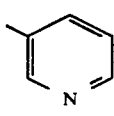 |
| 2 | H | —CH(OH)CH$_3$ | Na | Cl | 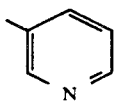 |
| 3 | H | —CH(OH)CH$_3$ | Na | Br | 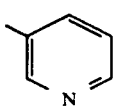 |
| 4 | H | —CH(OH)CH$_3$ | Na | I | 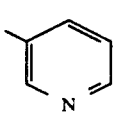 |
| 5 | H | —CH(OH)CH$_3$ | Na | SMe | 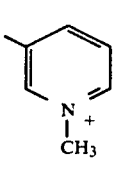 |
| 5a | H | —CH(OH)CH$_3$ | (−) | SMe | 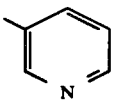 |
| 6 | H | —CH(OH)CH$_3$ | Na | S(O)Me | 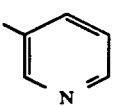 |
| 7 | H | —CH(OH)CH$_3$ | Na | SO$_2$Me | 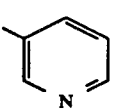 |
| 8 | H | —CH(OH)CH$_3$ | Na | F | 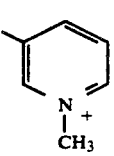 |
| 9 | H | —CH(OH)CH$_3$ | (−) | H |  |

TABLE I-continued (I')

[Structure: carbapenem core with R, R², COOM, phenyl bearing HET.ARYL–R^b and R^a]

| No. | R | R² | M | R^a | HET. ARYL–R^b |
|---|---|---|---|---|---|
| 10 | H | —CH(OH)CH₃ | Na | H | 3-pyridinyl N-oxide |
| 11 | H | —CH(OH)CH₃ | (−) | F | N-methyl-3-pyridinium |
| 12 | H | —CH(OH)CH₃ | Na | F | 3-pyridinyl N-oxide |
| 13 | H | —CH(OH)CH₃ | (−) | Br | N-methyl-3-pyridinium |
| 14 | H | —CH(OH)CH₃ | Na | Br | 3-pyridinyl N-oxide |
| 15 | H | —CH(OH)CH₃ | (−) | I | N-methyl-3-pyridinium |
| 16 | H | —CH(OH)CH₃ | Na | I | 3-pyridinyl N-oxide |
| 17 | H | —CH(OH)CH₃ | (−) | Cl | N-methyl-3-pyridinium |

TABLE I-continued
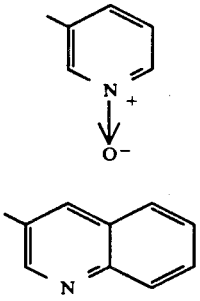
(I')
| No. | R | R² | M | Rᵃ | HET. ARYL—Rᵇ |
|-----|---|----|----|----|--------------|
| 18 | H | —CH(OH)CH₃ | Na | Cl | 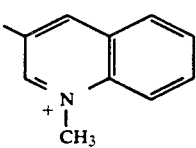 |
| 19 | H | —CH(OH)CH₃ | Na | H | 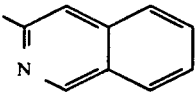 |
| 20 | H | —CH(OH)CH₃ | (—) | H | 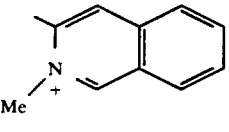 |
| 21 | H | —CH(OH)CH₃ | Na | H | 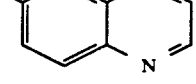 |
| 22 | H | —CH(OH)CH₃ | (—) | H | 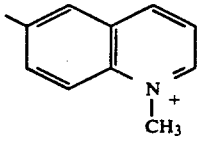 |
| 23 | H | —CH(OH)CH₃ | Na | H | 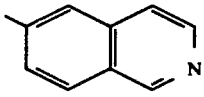 |
| 24 | H | —CH(OH)CH₃ | (—) | H | 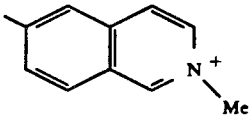 |
| 25 | H | —CH(OH)CH₃ | Na | H | |
| 26 | H | —CH(OH)CH₃ | (—) | H | |
| 27 | H | —CH(OH)CH₃ | Na | I | 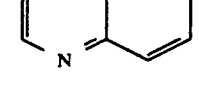 |

TABLE I-continued
| No. | R | $R^2$ | M | $R^a$ | HET. ARYL—$R^b$ |
|---|---|---|---|---|---|
| 28 | H | —CH(OH)CH$_3$ | (—) | I | 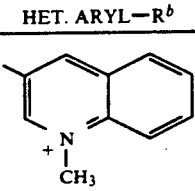 |
| 29 | H | —CH(OH)CH$_3$ | Na | I | 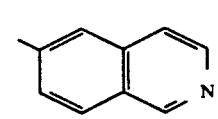 |
| 30 | H | —CH(OH)CH$_3$ | (—) | I | 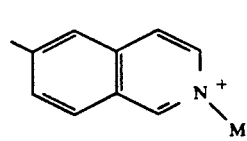 |
| 31 | H | —CH(OH)CH$_3$ | Na | H | 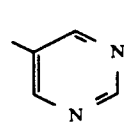 |
| 32 | H | —CH(OH)CH$_3$ | Na | I | 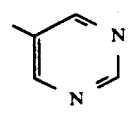 |
| 33 | H | —CH(OH)CH$_3$ | Na | H | 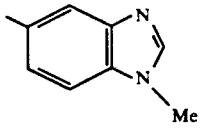 |
| 34 | H | —CH(OH)CH$_3$ | Na | CN | 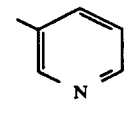 |
| 35 | H | —CH(OH)CH$_3$ | Na | H | 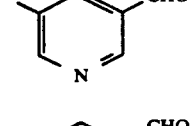 |
| 36 | H | —CH(OH)CH$_3$ | Na | I | 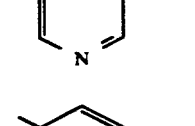 |
| 37 | H | —CH(OH)CH$_3$ | Na | H | 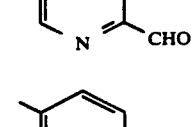 |
| 38 | H | —CH(OH)CH$_3$ | Na | I | 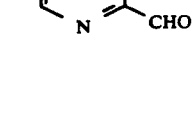 |

TABLE I-continued (I')

| No. | R | R² | M | Rᵃ | HET. ARYL—Rᵇ |
|---|---|---|---|---|---|
| 39 | H | —CH(OH)CH₃ | (—) | I | 5-CHO-1-methylpyridinium-3-yl |
| 40 | H | —CH(OH)CH₃ | Na | H | 2-amino-pyridin-5-yl |
| 41 | H | —CH(OH)CH₃ | (—) | H | 2-amino-1-methylpyridinium-5-yl |
| 42 | H | —CH(OH)CH₃ | (—) | I | 2-amino-1-methylpyridinium-5-yl |
| 43 | CH₃ | —CH(OH)CH₃ | Na | Br | pyridin-3-yl |
| 44 | CH₃ | —CH(OH)CH₃ | (—) | Br | 1-methylpyridinium-3-yl |
| 45 | CH₃ | —CH(OH)CH₃ | (—) | Br | pyridin-3-yl N-oxide |
| 46 | CH₃ | —CH(OH)CH₃ | Na | I | pyridin-3-yl |
| 47 | CH₃ | —CH(OH)CH₃ | (—) | I | 1-methylpyridinium-3-yl |

TABLE I-continued (I')

| No. | R | R² | M | Rᵃ | HET. ARYL—Rᵇ |
|---|---|---|---|---|---|
| 48 | H | —CH(F)CH₃ | (—) | I | 5-methyl-1-methylpyridinium (3-yl) |
| 49 | H | —CH(F)CH₃ | Na | I | 5-methylpyridin-3-yl |
| 50 | H | —CH(F)CH₃ | Na | I | 5-methyl-pyridin-3-yl, CHO |
| 51 | H | —CH(OH)CH₃ | Na | H | 5-methylpyridin-3-yl, SO₂Me |
| 52 | H | —CH(OH)CH₃ | Na | H | 5-methylpyridin-3-yl, SMe |
| 53 | H | —CH(OH)CH₃ | Na | H | 5-methylpyridin-3-yl, S(O)Me |
| 54 | H | —CH(OH)CH₃ | (—) | H | 5-methyl-1-methylpyridinium-3-yl, SMe |
| 55 | H | —CH(OH)CH₃ | (—) | H | 5-methyl-1-methylpyridinium-3-yl, Br |
| 56 | H | —CH(OH)CH₃ | (—) | H | 5-methyl-1-methylpyridinium-3-yl, S(O)Me |
| 57 | H | —CH(OH)CH₃ | (—) | H | 5-methyl-1-methylpyridinium-3-yl, SO₂Me |

TABLE I-continued
(I′)
| No. | R | R² | M | Rᵃ | HET. ARYL—Rᵇ |
|---|---|---|---|---|---|
| 58 | H | —CH(OH)CH₃ | Na | H | 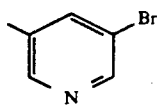 3-Br, 5-Me pyridine |
| 59 | H | —CH(OH)CH₃ | Na | SO₂Me | 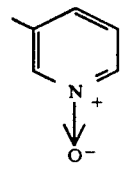 5-Me pyridine N-oxide |
| 60 | H | —CH(OH)CH₃ | (—) | I | 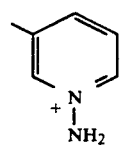 5-Me, N-NH₂ pyridinium |
| 61 | H | —CH(OH)CH₃ | K | H | 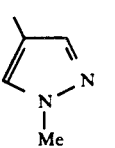 4-Me, N-Me pyrazole |
| 62 | H | —CH(OH)CH₃ | K | H | 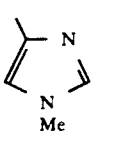 5-Me, N-Me imidazole |
| 63 | H | —CH(OH)CH₃ | K | H | 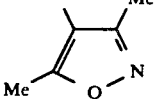 3,4,5-triMe isoxazole |
| 64 | CH₃ | —CH(OH)CH₃ | Na | Br | 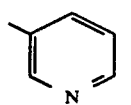 3-Me pyridine |
| 65 | CH₃ | —CH(OH)CH₃ | (—) | Br | 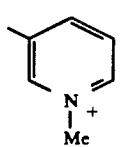 5-Me, N-Me pyridinium |
| 66 | CH₃ | —CH(OH)CH₃ | Na | Br | 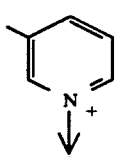 5-Me pyridine N-oxide |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethyl silyl, phenacyl, p-methoxybenzyl, acetonyl, o-nitrobenzyl, 4-pyridylmethyl, and $C_1$–$C_6$ alkyl such as methyl, ethyl or t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage fomr in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar indentity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 timer per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Aplications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are intended to be illustrative and not limiting.

All temperatures are in degrees Celsius.

STARTING MATERIAL SYNTHESIS

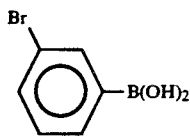

3-BROMOPHENYLBORONIC ACID

N-butyllithium (2.5M) (44 mL; 0.11M) was added dropwise over 15 mins. to a vigorously stirred solution of m-dibromobenzene (25G; 0.106M) in 500 mL of anhydrous ether at −78° under nitrogen. After stirring 10 mins. more, a solution of triisopropylborate (25.3 mL; 0.11M) in anhydrous ether (200 mL) was added over 20 mins. The cooling bath was then removed and the stirring solution was allowed to warm to R.T. over ~2 hrs. A small amount of solid separated. After stirring 15 mins. more at R.T., 150 mL of ice cold 8% aqueous hydrochloric acid was cautiously added, and the stirring was continued for 15 mins. The organic phase was separated, washed with 2×100 mL of a saturated sodium chloride solution, and dried over anhydrous magnesium sulfate. Solvent removal gave ~30 G of crude product as a semi-solid, which was shaken well with 150 mL of hexane. The solid was filtered and washed with 2×25 mL of hexane. The resulting silky solid (mp 178°-9° C. after softening at ~160° C.) (6.5 G) was used as 3-bromophenylboronic acid with a small amount of contamination. The hexane filtrate was concentrated and the residue was stirred well with 150 mL of petroleum ether (30°-60° C.). The resulting solid was filtered and washed with 2×25 mL of petroleum ether. This resulting solid (4.4G) melting at 178.3°-179° C. was the desired 3bromophenylboronic acid.

NMR: 7.38-7.46; 7.70-7.80; 8.1-8.18; 8.31 (aromatic H's)

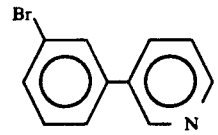

3-(3'-BROMOPHENYL)PYRIDINE

Tetrakis-(triphenylphosphine)palladium (153 mG; 0.135 mM) was added to a stirred solution of 3-bromopyridine (0.434 mL; 4.5 mM) in 9 mL of toluene. The resulting solution was stirred 10 mins. under nitrogen at R.T. 2M aqueous sodium carbonate solution (5 mL; 10 mM) followed by a solution of 3-bromophenylboronic acid (1 G; 5 mM) in 2.5 mL of absolute ethanol were added. This heterogeneous reaction mixture was vigorously stirred 20 hrs. at 80° under nitrogen, cooled, diluted with 25 mL of methylene chloride, and washed with 2×5 mL of 2M aqueous sodium carbonate solution containing 0.5 mL of conc. ammonia. The organic layer was dried over anhyd. magnesium sulfate. Solvent removal followed by purification on silica gel using ether:petroleum ether (1:1) as solvent gave 3-(3'-bromophenyl)pyridine in 35% yield as a colorless liquid boiling at 140°-2°/~2 mm.

NMR: 7.25-7.90 (aromatic H's); 8.63 and 8.82 (H's α-to nitrogen of pyridine)

MS: M+ =234

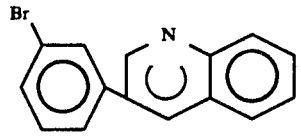

3-(3'-BROMOPHENYL)QUINOLINE

The quinoline was prepared as above using 3-bromoquinoline instead of 3-bromopyridine. 42% yield.

NMR: 9.1 (H α to nitrogen of quinoline); 7.23-8.27 (aromatic H's)

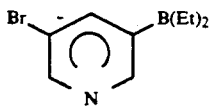

3-(5'BROMOPYRIDYL)DIETHYLBORANE 7.11 g (30 mmol) of 3,5-dibromopyridine was added to 150 ml of ether stirring vigorously at −78° C. After 5 min., 12.6 ml of n-butyllithium (2.8M in hexanes) was added slowly and the reaction turned honey yellow in color. After 30 min. 63 ml (63 mmol, 2.1 equiv) of 1M diethylmethoxyborane in THF was added slowly and the reaction was allowed to slowly warm to RT and stirred overnight.

A white solid had precipitated and it was collected by filtration (a). The yield was 2.95 g. NMR (200 mg Hz, $CDCl_3$) looked very clean. The filtrate was partitioned with EtoAC and sat'd NaCl. The organic layer was dried ($MgSO_4$), and concentrated to a brown residual solid. Triteration with $Et_2O$ and filtration (b) gave 1.51 g. 200 Mg Hz NMR ($CDCl_3$) looked good. Yield (a)+(b)=4.46 g 19.74 mmol, 66% yield. A 3rd crop was obtained from the filtrate of (b) 0.53 mg. TLC (hexane) weak UV spot at origin.

NMR: 0.4-0.72 ($BCH_2CH_3$'s); 7.48, 7.91, & 8.13 (pyridine H's)

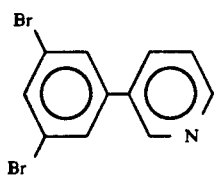

3-(3',5'-DIBROMOPHENYL)PYRIDINE

Tetrakis-(triphenylphosphine)palladium (915 mG; 0.75 mM) was added to a stirred solution of 1,3,5-tribromobenzene (6.3 G; 20 mM) in 75 mL of anhydrous tetrahydrofuran under nitrogen at R.T. After stirring 5 mins., tetra n-butyl ammonium bromide (483 mG; 1.5 mM), followed by powdered potassium hydroxide (2.52 G, 45 mM) and 3-pyridyldiethyl borane (2.2 G; 15 mM) were added in that order. The resulting reaction mixture was heated to reflux 2 hrs., cooled, diluted with 100 mL of ethyl acetate, washed with 10×25 mL of sat'd. sodium chloride solution, and dried over anhyd. magnesium sulfate. Solvent removal, and purification on silica gel using ethyl acetate:hexane (2:3) mixture as solvent gave 1.9 G of 3-(3',5'-dibromophenyl)pyridine as a colorless oil boiling at 137°-139°/~1 mm, which slowly became a glassy solid.

NMR δ: 7.36-7.43; 7.78-7.86; 8.64 & 8.78 (pyridine) 7.72 & 7.78-7.86 (phenyl H's)

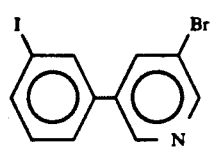

3-BROMO-5-(3'-IODOPHENYL)PYRIDINE

The pyridine was prepared as above using 1,3-diiodobenzene and 3-(5-bromo)pyridyl diethylborane NMR: 8.69 & 8.71 (H's α to nitrogen of pyridine) 7.0-8.0 (aromatic H's)

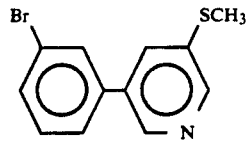

3-METHYLTHIO-5-(3'-BROMOPHENYL)PYRIDINE

The pyridine was similarly obtained from 1,3-dibromobenzene and 3-(5-methylthio)pyridyl diethylborane.

NMR: 2.56 ($SCH_3$, s); 8.51 & 8.55 (H's α to nitrogen of pyridine) 7.26-7.7 (aromatic H's).

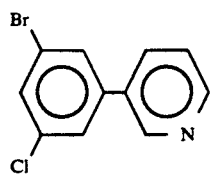

3-[[(3'-BROMO)-(5'-CHLORO)]PHENYL]PYRIDINE

The pyridine was prepared as above from 3,5-dibromochlorobenzene and 3-pyridyldiethylborane.

NMR: 8.65 & 8.8 (H's α to pyridine nitrogen) 7.32-7.66 (aromatic H's).

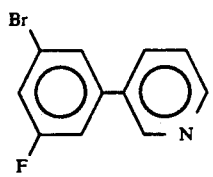

3-[[(3'-BROMO)-(5'-FLUORO)]PHENYL]PYRIDINE

The pyridine was prepared as above from 3,5-dibromo-fluorobenzene and 3-pyridyldiethylborane NMR: 8.62 & 8.77 (H's α to pyridine nitrogen) 7.14-7.82 (aromatic H's).

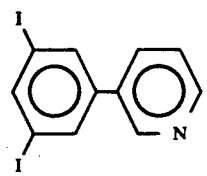

3-(3',5'-DIIODOPHENYL)PYRIDINE

The pyridine was prepared as above from 1,3,5-triiodobenzene and 3-pyridyldiethylborane.

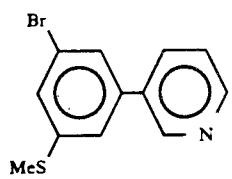

3[[(3'-BROMO)-5'-METHYLTHIO)]PHENYL]-PYRIDINE

Similarly, 3,5-dibromothioanisole (2 equivalents) and 3-pyridyl diethylborane (1 mole equivalent) gave a 55% yield of 3-[[(3'-bromo)-(5'-methylthio))]phenyl]pyridine as an oil.

NMR SCH$_3$: 2.54(s); 7.25–8.84 (aromatic H's)

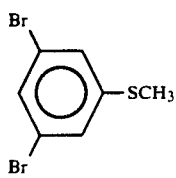

3,5-DIBROMOTHIOANISOLE

A 2.5M solution of n-butyllithium (42 mL; 0.105M) was added over 25 mins. to a vigorously stirred suspension of 1,3,5-tribromobenzene (31.5 G; 0.1M) in 1.6 L of anhydrous ether and 400 mL of anhydrous tetrahydrofuran under nitrogen at −78°. After stirring the mixture 30 minutes, 2 equivalents of dimethyldisulfide was added dropwise. The resulting mixture was stirred at R.T. overnight. 150 mL of sat'd sodium chloride solution was cautiously added. 500 mL of ethyl acetate was added. The organic phase was separated, and dried over anhyd. magnesium sulfate. Solvent removal gave a crude product, which was purified on silica gel using hexane as solvent. The desired product was isolated and distilled at 107°-110°/~1 mm to give 18 G of 3,5-dibromothioanisole as a colorless liquid, which slowly solidified on standing.

NMR: 2.49 (SCH$_3$, s); 7.3 & 7.43 (aromatic H's)

M-BROMOPHENACYL BROMIDE

In a fashion analogous to that of Cowper and Davidson, *Org. Syn. Coll. Vol.*, 2, 480–1 (1943) for the conversion of acetophenone to phenacyl bromide, m-bromoacetophenone (5 g, 25 mmol) was converted to m-bromophenacyl bromide. Although begun at 0°, the reaction mixture was allowed to warm to ambient temperature in order to achieve the desired decoloration (reaction) of the added bromine. After removal of solvent and HBr with a water aspirator, the oily residue was partitioned between Et$_2$O and H$_2$O. The organic layer was then washed with brine and concentrated under house vacuum to give crude product, pure enough for further reaction.

Some crude product was chromatographed on silica gel (eluting with 10% CH$_2$Cl$_2$ in hexane), and the purified fractions were recrystallized (hexane) to give a first crop of m-bromophenacyl bromide (2 g white needles, 29% yield) and then a second crop (1.1 g, 16% yield) of m-bromophenacyl bromide.

$^1$H NMR (300 MHz, CDCl$_3$) δ4.42 (s, CH$_2$Br); 7.39, 7.55, 7.82 and 8.12 (4-m's, 4 arom. H's).

4-M-BROMOPHENYLIMIDAZOLE

By analogy to the conversion of phenacyl bromide to 4-phenylimidazole (Brederick, H. and Theilig G., *Chem. Ber.*, 86, 88–96 (1953)), m-bromophenacyl bromide (2 g, 7.2 mmol) was converted to 4-m-bromophenylimidazole. The tan precipitate produced upon work-up was dissolved in CH$_2$Cl$_2$, and the solution was dried (MgSO$_4$) and then reconcentrated to give the crude product (922 mg). Recrystallization of a portion from CH$_2$Cl$_2$ provided pure 4-m-bromophenylimidazole.

$^1$H NMR (300 MHz, CDCl$_3$) δ7.22, 7.39, 7.70 (3 m's, phenyl H's, and H$_5$ of imidazole); 7.92 (br. s, H$_2$ of imidazole).

4-M-BROMOPHENYL-1-METHYLIMIDAZOLE

Using the method of Hazeldine et al., *J. Chem. Soc.*, 125, 1431–41 (1924) a mixture of dimethylsulphate (145 μl, 1.53 mmol) and 4-m-bromophenyl imidazole (341 mg; 1.54 mmol) was stirred under N$_2$ until the reaction mixture became extremely viscous. Toluene (150 μl) was added, and the mixture was heated at 100° C. for 1 hour. After cooling to ambient temperature, H$_2$O (5 ml) was added, and the reaction mixture was brought to pH 9 with NaOH solution. It was then extracted with CH$_2$Cl$_2$ (2×10 ml). The organic layers were washed with brine, dried (MgSO$_4$), and concentrated in vacuo to give 262 mg crude product mixed with starting material. Purification using preparative TLC on 2-1000μ Si Gel GF plates (eluting with 5% MeOH in CH$_2$Cl$_2$ and extracting with 10% MeOH in CH$_2$Cl$_2$) provided the product, 4-m-bromophenyl-1-methylimidazole (121 mg, 33% yield) as the least polar band.

$^1$H NMR (300 MHz, CDCl$_3$) δ3.72 (s, N-CH$_3$), 7.17–7.36 (m, 3-phenyl H's), 7.46 (br. s, 1-imidazole H), 7.67 (m, 1-phenyl H), 7.91 (br. s, 1-imidazole H).

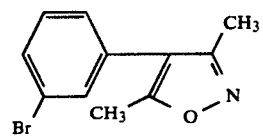

4-M-BROMOPHENYL-3,5-DIMETHYLISOXAZOLE

The reaction of 3,5-dimethyl-4-iodoisoxazole (Kochetkov, N. K. *Zhurnal Obschchie Khimii*, 31, 2167–2172 (1961)) (2.4 g, 11 mmol) with 3-bromophenylboronic acid (2.24 g, 11 mmol) using the procedure for the preparation of 3-(3'-bromophenyl)pyridine gave 3.3 g crude 4-m-bromophenyl-3,5-dimethylisoxazole. After a quick filtration on Si gel (eluting with CH$_2$Cl$_2$), the material was further purified by preparative TLC on 12-1000μ Si Gel GF plates (eluting with 10% acetone/hexane and extracting with 10% MeOH/CH$_2$Cl$_2$), to provide 1.2 g of the arylated isoxazole. Sublimation (ambient to 70° C., high vacuum) of 0.5 g provided 404 mg of analytically pure material.

$^1$H NMR (300 MHz, CDCl$_3$) δ2.24 and 2.38 (2 s's, isoxazole methyls), 7.14–7.48 (m's phenyl protons).

Anal. Calcd for C$_{11}$H$_{10}$BrNO: C, 52.40; H, 4.00; Br, 31.70; N, 5.56. Found: C, 52.25; H, 3.68; Br, 31.82; N, 5.24.

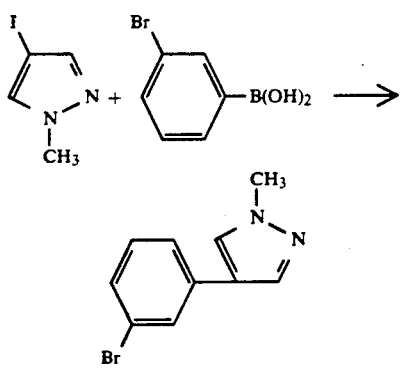

1-METHYL-4-(3'-BROMOPHENYL)PYRAZOLE

The reaction of 1-methyl-4-iodopyrazole (Liljefors, S., and Gronowitz S. *Chemica Scripta*, 15, 102-9 (1980)) (1.3 g, 6.2 mmol) with 3-bromophenyl boronic acid (1.24 g, 6.2 mmol) using the procedure for the preparation of 3-(3'-bromophenyl)pyridine gave crude 4-(m-bromophenyl)-1-methylpyrazole which was chromatographed on a column of Bakers Silica Gel (60–200 mesh) packed and eluted with $CH_2Cl_2$. The less polar fractions contained undesired, incorrectly coupled products while the later more polar fractions contained the desired product (0.82 g, 56% yield).

$^1$H NMR (300 MHz, $CDCl_3$) δ3.94 (s, N-$CH_3$); 7.20–7.40 (m's, phenyl H's); 7.61 & 7.72 (3H, 2-pyrazole H's & 1-phenyl H).

MS: m/e 238,236 (M+)

Approximately 200 mg of this material was further purified by preparative TLC on 3–1000µ Si Gel GF plates (eluting with 20% acetone/hexane and extracting with 10% $MeOH/CH_2Cl_2$) to provide 161 mg pure 4-(m-bromophenyl)-1-methylpyrazole for the subsequent Grignard reaction.

STEP A: GENERAL SYNTHESIS OF ARYLKETONES

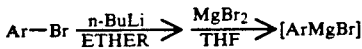

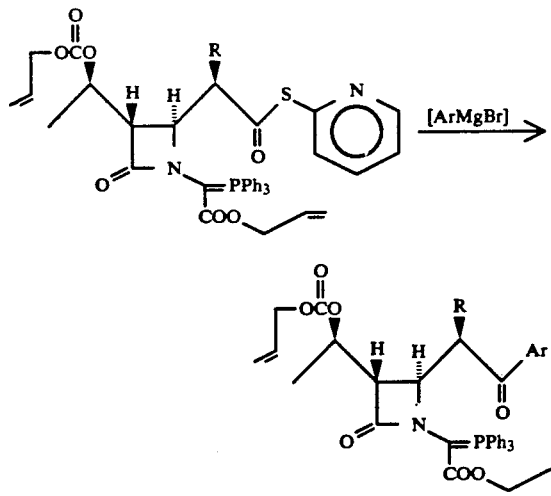

Aryl bromide (3 mM) was added to anhydrous ether (12 mL) at −78° under nitrogen. n-Butyllithium (2.5 molar solution; 1.32 mL; 3.3 mM) was added dropwise to the above stirred suspension of aryl bromide. The resulting mixture was stirred 0.5 hr at −78°. A solution of magnesium bromide freshly prepared by stirring 6.6 mM of magnesium turnings in 24 mL of anhydrous tetrahydrofuran with 6 mM of 1,2-dibromoethane for about 1 hr under nitrogen at ambient temperature, was then added dropwise to the above stirring lithium salt at −78°. The resulting mixture was stirred 15 mins at −78°, and 30 mins at 0°. A turbid solution was obtained which was used as a 0.0833 molar solution of the required aryl magnesium bromide.

This solution of the Grignard reagent was added slowly to a stirred solution of 1.4 mM of (3S, 4R)-1-[[allyloxy)carbonyl](triphenylphosphoranylidene)methyl]-3-[(1R)-1-[(allyloxy)carbonyloxy]ethyl]-2-[[(2'-pyridylthio)carbonyl]alkyl]azetidin-2-one in 5 mL of anhydrous tetrahydrofuran at 0° under nitrogen. The reaction mixture was stirred 15 mins. at 0°, and sat'd ammonium chloride (15 mL) and 30 mL of ethyl acetate were added. The organic layer was separated, washed with 2×15 mL of sat'd. sodium chloride solution, and dried over anhydrous magnesium sulfate. Solvent removal and purification on silica gel using mixtures of ethyl acetate:hexane, acetone:hexane, or other suitable solvents gave the desired aryl ketone as a light yellow foam.

STEP B1: GENERAL PROCEDURE FOR CYCLIZATION:

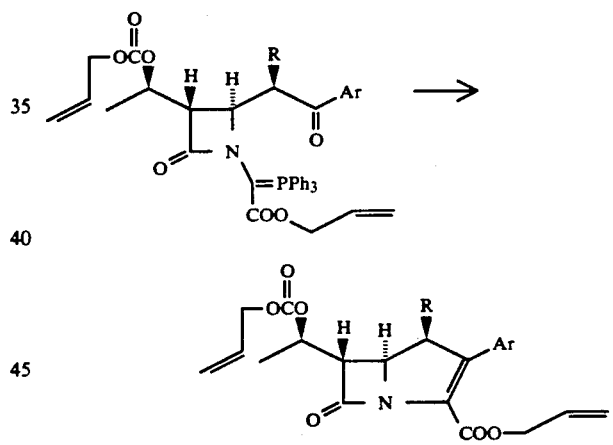

A solution of the ylid ketone (0.25 mM) in 2 mL of p-xylene containing a tiny crystal of hydroquinone was heated 45 mins. to 3 hours (depending on the nature of R) at 130° C. under nitrogen. The solution was cooled, applied to a silica gel column packed with hexane and then eluted first with hexane and then with 4:1 to 2:3 mixtures of hexane:ethyl acetate to give the desired carbapenem analogs.

STEP B2: GENERAL PROCEDURE FOR THE SYNTHESIS OF PYRIDINIUM ZWITTERIONS OF CARBAPENEMS

Methyl trifluoromethane sulfonate (0.3 mM) was added to a solution of pyridyl carbapenem (0.25 mM) in 3 mL of anhydrous methylene chloride under nitrogen at 0°. After 1 hour stirring, solvent and excess methylating agent were removed in vacuo at room temperature. The resulting pale yellow foam was deallylated following the procedure employed for the following examples except for the solvent system. In this case, a 3:1 mixture of methylene chloride and ether was used.

STEP B3: GENERAL PROCEDURE FOR THE OXIDATION OF PYRIDINE TO PYRIDINE N-OXIDE

To a vigorously stirred solution of pyridyl carbapenem (0.2 mM) were added 1.6 mL of a 0.5M solution of sodium bicarbonate followed by 0.5 mM of m-chloroperbenzoic acid. This reaction mixture was stirred 1 hour at R.T. 5 mL of a 5% solution of sodium thiosulfate was added, and stirring was continued for 1 hour. After diluting with 10 mL of ethyl acetate, the reaction mixture was washed with 3×5 mL of saturated sodium chloride solution, dried over anhydrous magesium sulfate. Solvent removal gave a crude oil, which was chromatographed on silica gel using hexane:ethyl acetate (2:7) mixture to give the desired carbapenem pyridine N-oxide.

STEP B4: PREPARATION OF SULFOXIDES AND SULFONES IN THE PRESENCE OF A PYRIDINE MOIETY

Following the above procedure, a sulfide was oxidized preferentially to sulfone in the presence of a pyridine moiety.

a): Using only 1.5 equivalents of m-chloroperbenzoic acid, the same sulfide was oxidized preferentially to sulfoxide.

b): 4.5 equivalents of m-chloroperbenzoic acid produced sulfone pyridine N-oxide.

STEP C: GENERAL PROCEDURE FOR DEALLYLATION

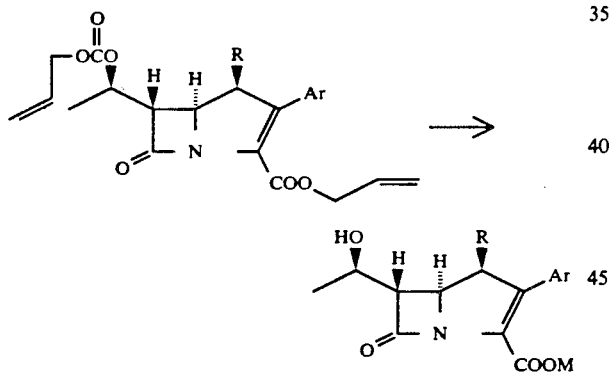

To a stirred solution of the carbapenem (0.2 mM) in 3 mL of a 1:1 mixture of methylene chloride:ether in a centrifuge tube at 0° under nitrogen were added 2-ethylhexanoic acid (0.2 mM), triphenylphosphine (0.05 mM), tetrakis-(triphenylphosphine)palladium (0.04 mM), and 0.2 mM of sodium or potassium 2-ethylhexanoate. This mixture was stirred 2 hrs when a solid precipitated out. After diluting with 10 mL of ether, the mixture was centrifuged and the supernatant liquid was decanted. The remaining solid was stirred with 2 mL of ethyl acetate and centrifuged. The resulting solid was dissolved in 1 mL of water and applied to a 1000 μ reverse phase silica gel plate. Elution with 1:9 to 1:3 mixtures of acetonitrile:water gave an ultraviolet active area, which was scraped and stirred with 5 mL of 4:1 acetonitrile:water mixture. The solid was filtered and washed with 3×2 mL of a 4:1 acetonitrile:water mixture. The filtrate was washed with 4×10 mL of hexane, concentrated to 1 mL in vacuo at R.T. and lyophilized to give the sodium or potassium salt of the carbapenem as a white to creamy, fluffy mass.

In the following examples, the process steps refer to the above General Procedures, Steps A-C.

The IR data are in cm$^{-1}$.

The UV data are in nanometers for $\lambda_{max}^{water}$.

The NMR data are recorded in δ in CDCl$_3$ unless otherwise specified.

EXAMPLE 1

STEP A

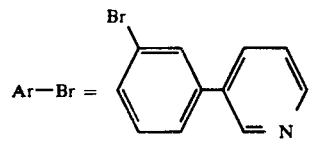

Conditions:
1) n-BuLi/THF; −78°; ether; 0.5 hr.
2) MgBr$_2$/THF
3) 0°; 20 min.; pyridylthioester Yield: 27%

STEP B

Conditions: Xylene; 130°; 3 hrs.
Yield: 65%
Spectra:
IR: 1780; 1740; 1715
NMR:
H6: 3.42–3.5; dd; J=3 & 8.5 Hz
H5: 4.26–4.4; ddd; J=3, 9 & 10 Hz

STEP C

M=Na$^+$
Conditions: Pd(PPh$_3$)$_4$; PPh$_3$;

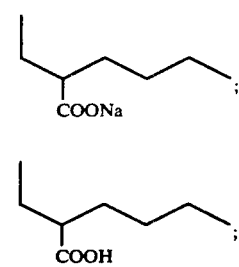

CH$_2$Cl$_2$:Et$_2$O; 0°; 2 hrs.
Yield: 77%
Spectra:
UV: 300
εext: 6245

EXAMPLES 2, 17 and 18

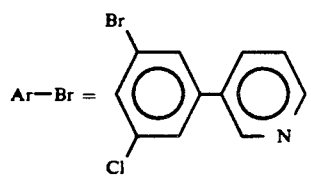

STEP A

Conditions:
1) BuLi/-31 78°/Ether
2) MgBr₂/THF
3) Pyridylthioester/THF/0°/15 min.

Yield: ~60%
Spectra:
IR: 1740; 1685; 1640; 1620

STEP B

Step B1: Cyclization of the ylide ketone to the carbapenem
Step B2: N-Methylation of the pyridine of the carbapenem
Step B3: N-oxidation of the pyridine of the carbapenem B1:
Conditions: Xylene; 140°; 1 hr
Yield: 445 mg from 880 mg of ylide ketone
Spectra:
IR: 1780; 1740; 1720
NMR:
  H6: 3.42-3.48; dd; J=3 & 8.5 Hz
  H5: 4.26-4.38; ddd; J=3, 8.5 & 10 Hz B2:
Conditions: CF₃SO₃CH₃; CH₂Cl₂; 0°; 1 hr Crude product was used in deallylation
Spectra:
NMR: ⁺N-CH₃: 4.52 (s)

B3:
Conditions: mCPBA; 1 hr; NaHCO₃: 0°-20°
Yield: ~70%
Spectra:
IR: 1780; 1740; 1720
NMR: H6: 3.44-3.50; dd; J=3 & 8.5 Hz H5: 4.28-4.40; ddd; J=8.5 & 10 Hz

STEP C

Conditions: Pd(PPh₃)₄; PPh₃

CH₂Cl₂:Ether; 0°; 2 hrs
Yield: ~55% of 2
Spectra:
UV: ~302
ε: 9756
Yield: ~28% of 17
Spectra:
ε: 8289
Yield: ~22% of 18
Spectra:
UV: ~300
ε: 7859

EXAMPLES 3 and 14

STEP A

Conditions:
1) n-BuLi/−78° Ether; 0.5 hr.
2) MgBr₂/THF
3) 0°; 15 min.; pyridylthioester Yield: 71%
Spectra:
IR 1740; 1685; 1640; 1620

STEP B

Step B1: cyclization of ylide ketone to carbapenem
Step B2: oxidation of pyridine to pyridine N-oxide B1
Conditions: Xylene; 140°; 30 min.
Yield: 90%
Spectra:
IR: 1780; 1745; 1720
NMR:
  H6: 3.42-3.48; dd; J=3 & 8.5 Hz
  H5: 4.26-4.38; ddd; J=3, 8.5 & 10 Hz B2
Conditions: mCPBA; 2 eq.; NaHCO₃; CH₂Cl₂
Yield: 47% of N-oxide
Spectra:
NMR:
  H6: 3.40-3.48; dd; J=3 & 8 Hz
  H5: 4.24-4.38; ddd; J=3, 9 & 10 Hz

STEP C

M = Na⁺
Conditions: Pd(PPh₃)₄; PPh₃;

CH₂Cl₂:Et₂O; 2 hrs.; 0°
Yield: 20% of 3
Spectra:
UV: 303
ε ext: 7306
Yield: 45% of 14
Spectra:
UV 303
εext: 6818

EXAMPLES 4, 15 and 16

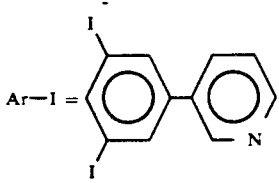

STEP A

Conditions:
1) n-BuLi/Ether/−78°/30 min
2) MgBr₂/THF
3) Pyridylthioester/0°/15 mins/THF Yield: ~42% of ylide ketone
Spectra:
IR: 1740; 1680; 1640; 1620

STEP B

STEP B1: Cyclization of the ylide ketone to the carbapenem
STEP B2: N-methylation of pyridine of the carbapenem
STEP B3: N-oxidation of pyridine of the carbapenem B1:
Conditions: Xylene/140°/1 hr
Yield: ~79%
Spectra:
IR: 1780; 1740; 1720
NMR:
  H6: 3.42-3.48; dd; J=3 & 8 Hz
  H5: 4.26-4.38; ddd; J=3,8 & 10 Hz B2:
Conditions: CF₃SO₃CH₃/0°/CH₂Cl₂/1 hr The crude product was used in deallylation.

B3:
Conditions: mCPBA; NaHCO₃; 1 hr; 0°-20°
Yield: ~63%
Spectra:
IR: 1780; 1740; 1720
NMR:
  H6: 3.42-3.48; dd, J=3 and 8 Hz
  H5: 4.26-4.38; ddd, J=3, 8 and 10 Hz

Step C

Conditions: Pd(PPh₃)₄; PPh₃

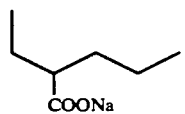

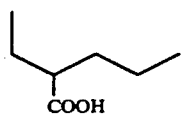

CH₂Cl₂:Ether; 0°; 2 hrs
Yield: ~55% of 4
Spectra:
UV: ~303
ε: 8964
Yield: ~21% of 15
Spectra:
UV: ~300
ε: 6579
Yield: ~38% of 16
Spectra:
UV: ~295
ε: 8036

EXAMPLE 5

Step A

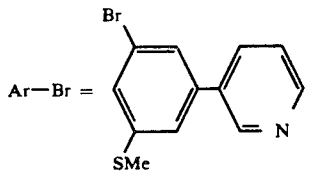

Conditions:
1) n-BuLi/−78°; Ether
2) MgBr₂THF
3) 0°; 15 min.; pyridylthioester

Yield: 44%
Spectra:
IR 1745; 1685; 1645; 1620

Step B

Conditions: Xylene; 140°; 1.75 hrs.
Yield: 66%
Spectra:
IR: 1780; 1745; 1720
NMR:
  SCH₃ : 2.54(s)
  H: 3.4-3.5; dd; J=3 & 8 Hz
  H5: 4.25-4.38; ddd; J=3, 9 & 10 Hz

Step C

M=Na⁺
Conditions: Pd(PPh₃)₄; PPh₃;

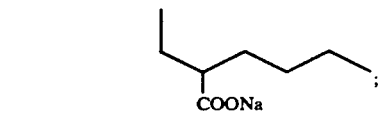

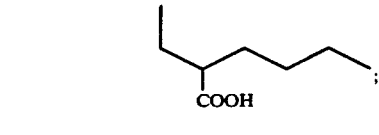

CH₂Cl₂:Ether; 0°; 0 hrs.
Yield: 66%
Spectra:
UV: 305
ε ext: 9363

EXAMPLE 5a

Step A

Conditions:
1) n-BuLi; −78°; ether
2) MgBr₂/THF
3) 0°; 15 min; pyridylthioester

Yield: 44%

Step B

Step B1: cyclization of ylike ketone or carbapenem
Step B2: quaternization of pyridine of carbapenem
B1
Conditions: Xylene; 140°; 1.75 hrs.
Yield: 62%
B2
Conditions: CF₃SO₃CH₃; CH₂Cl₂ ; 0°; 1 hr.
Spectra:
NMR (crude):
SCH₃ : 2.52(s)
N+CH₃ : 4.47(s)
H6: 3.60–3.68; dd; J=3 & 8 Hz
5: 4.29–4.32; ddd, J=3, 9 & 10 Hz The product from this step was used in Step C without further purification.

Step C

Conditions: Pd(PPh₃)₄; PPh₃;

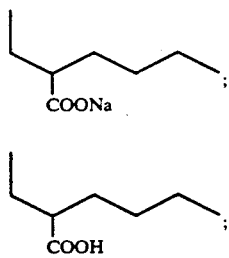

CH₂Cl₂ ; 0°; 2 hrs.
Yield: 181 %
Spectra:
UV 300
ε ext: 6888

EXAMPLES 6, 7 AND 59

Step A

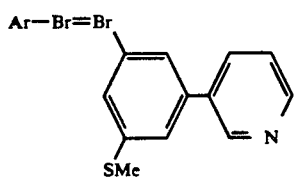

Conditions:

1) n-BuLi/−78°; ether
2) MgBr₂/THF
3) 0°; 15 min; pyridylthioester
Yield: 44%

Step B

Step B1: cyclization of ylike ketone to carbapenem
Step B4a: preparation of sulfoxide of carbapenem
Step B4b: preparation of sulfone and sulfone N-oxide of carbapenem
B1
Conditions: Xylene; 140°; 1.75 hrs.
Yield: 66%
B4a
Conditions: mCPBA; 1.25 eq.; NaHCO₃; CH₃Cl₂ ; 1 hour
Yield: 47% (sulfoxide)
Spectra:
NMR:
SCH₃ : 2.8(s)
H6: 3.4–3.48; dd; J=3 & 8 Hz
H5: 4.26–4.4; ddd; J=3, 9 & 10 Hz
B4b
Conditions: mCPBA; 2.5 eq.; NaHCO₃; CH₂Cl₂ ; 1 hour These conditions gave a separable mixture of two products: sulfone and sulfone N-oxide.
Yield: 54% (sulfone)
Spectra:
IR: 1785; 1745; 1725
NMR:
SCH₃ : 3.12(s)
H6: 3.26–3.38; dd, J=3 & 8 Hz
2 H5: 4.31–4.14; ddd; J=3, 9 & 10 Hz
Yield: 17% (sulfone N-oxide)
Spectra:
IR: 1790; 1750; 1720
NMR:
SCH₃ : 3.13(s)
H6: 3.45–3.54; dd; J=3 & 8 Hz
H5: 4.33–4.45; ddd; J=3, 9 & 10 Hz

Step C

Deallylation of sulfoxide, sulfone and sulfone N-oxide
M=Na+
Conditions: Pd(PPh₃)₄; PPh₃:

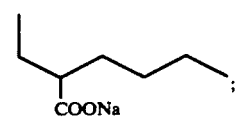

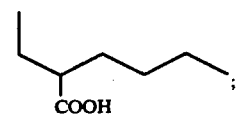

CH₂Cl₂:Ether; 0°; 2 hrs.
Yield: 59% (sulfoxide) of 6
UV: 305
ε ext: 9114
Yield: 49% (sulfone) of 7
Spectra:
UV: 308
ε ext: 9180
Yield: 38% (sulfone N-oxide) of 59
Spectra:

UV: 308
ε ext: 6338

EXAMPLES 8, 11 AND 12

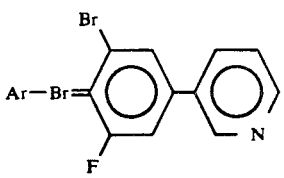

Step A

Conditions:
1) n-BuLi/−78°/ether
2) MgBr₂/THF
3) pyridylthioester; THF; 0°/15 min
Yield: ~53% of ylike ketone
IR: 1740; 1690; 1640; 1620

Step B

Step B1: Cyclization of ylike ketone to the carbapenem
Step B2: N-methylation of pyridine of carbapenem
Step B3: N-oxidation of pyridine of carbapenem B1
Conditions: xylene/140°/1 hr
Yield: ~77% of the carbapenem
Spectra:
IR: 1780; 1745; 1720
NMR:
 H6: 3.44–3.51; dd; J=3 & 8.5 Hz,
 H5: 4.29–4.4; ddd; J=3, 8.5 & 10 Hz B2
Conditions: CF₃SO₃CH₃ ; 0°; CH₂Cl₂ ; 1 hr Crude product was used in deallylation step.
Spectra:
NMR: ⁺N-CH₃ ; 4.52 (s)

B3
Conditions: mCPBA/NaHCO₃/CH₂Cl₂/0°-20°/ 1 hr
Yield: ~40% of pyridine N-oxide
Spectra:
IR: 1780; 1745; 1720
NMR: H6: 3.44–3.52; dd; J=3 & 8.5 Hz, H5: 4.28–4.39; ddd, J=3, 8.5 & 11 Hz

Step C

Conditions: Pd(PPh₃)₄; PPh₃

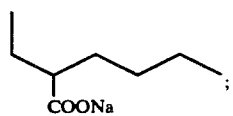

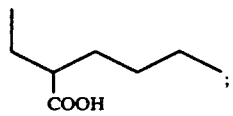

CH₂Cl₂:ether; 0°; 2 hrs
Yield: ~60% of 8
Spectra:
UV: ~304
ε: 8892
Yield: ~31% of 11

Spectra:
UV: ~295
ε: 7716
Yield: ~61 of 12
Spectra:
UV: ~300
ε: 9744

EXAMPLE 13

Step A

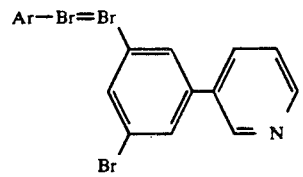

Conditions:
1) n-BuLi/−78°; Ether; 0.5 hr
2) MgBr₂/THF
3) 0°; 15 min.; pyridylthioester
71%

Step B

Step B1: cyclization of ylide ketone to carbapenem
Step B2: N-methylation of pyridine to N-methylpyridinium compound B1:
Conditions: Xylene; 140°; 30 min.
Yield: 90%

B2:
Conditions: CF₃SO₃CH₃; CH₂Cl₂; 0°; 1 hr.
Spectra:
NMR:
 H6: 3.58–3.64; dd; J=3 & 7 Hz
 H5: 4.24–4.38; ddd; J=3, 9 & 10 Hz
 N⁺CH₃: 4.48(s)

Step C

Conditions Pd(PPh₃)₄; PPh₃;

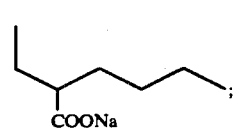

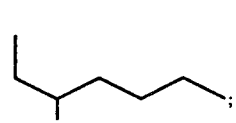

CH₂Cl₂; 2 hrs; 0°
Yield: 26%
UV: 293
ε ext: 6911

EXAMPLES 19 AND 20

Step A

Ar—Br = 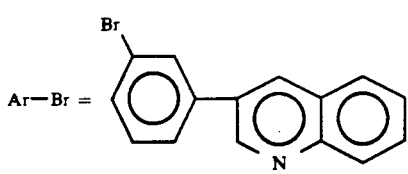

Conditions:
1) n-BuLi/ether/−78°/0.5 hr
2) MgBr₂/THF
3) 0°; 15 min; pyridylthioester.
Yield: 20% of ylide ketone

Step B

Step B1: Cyclization of ylide ketone to carbapenem
Step B2: N-methylation of quinoline of carbapenem
B1
Conditions: Xylene; 140°; 1 hr.
Yield: 35% of carbapenem
Spectra:
IR: 1780; 1745; 1720.
NMR:
  H6; 3.42–3.48; dd; J=3 & 8 Hz;
  H5; 4.26–4.38; ddd; J=3, 8 & 10 Hz.
B2
Conditions: CF₃SO₃CH₂; CH₂Cl₂; 0°; 1 hr. Crude product was used directly in deallylation.

Step C

Conditions: Pd(PPh₃)₄; PPh₃;

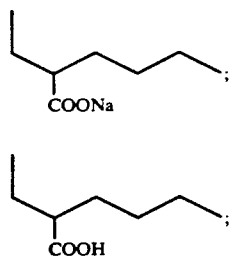

CH₂Cl₂: ether; 2 hrs; 0°
Yield: 53% of 19 (phenylquinoline)
Spectra of Example 19 (M=Na):
UV: 290
$\epsilon_{ext}$: 5086
Yield: 14% of 20 (N-methylquinolinium phenyl)
UV of Example 20 [M=(−)]
λ: 300
ε: 4725
NMR: 4.8 (+N-CH₃; s);

EXAMPLES 51, 52, 53, 54, 56 AND 57

Ar—Br = 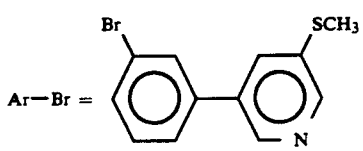

Step A

Conditions:
1) n-BuLi/ether/−78°/30 mins.
2) MgBr₂/THF
3) 0°/THF/pyridylthioester
Yield: 41% of ylide ketone

Step B

Step B1: Cyclization of the ylide ketone to the carbapenem
Step B4a & b: Oxidation of sulfide of carbapenem to sulfoxide and sulfone
Step B3: N-methylation of sulfide, sulfoxide and sulfone of pyridine
B1
Conditions: Xylene/140°/1 hr.
Yield: 73% of carbapenem
Spectra:
NMR:
  H6: 3.42–3.46; dd; J=3 & 8 Hz;
  H5: 4.26–4.38; ddd; J=3, 8 & 10 Hz.
B4a & b
Conditons: mCPBA (1.2 eq for sulfoxide; 2 eq for sulfone)/NaHCO₃/0°/1 hr.
Yield: 84% of sulfoxide
Spectra:
NMR: H6: 3.44–3.50; dd; J=3 & 8 Hz; H5: 4.28–4.30; ddd; J=3, 8 & 10 Hz
Yield: 68% of sulfone
Spectra:
NMR: H6: 3.42–3.48; dd; J=3 & 1.5 Hz; H5: 4.25–4.37; ddd; J=3, 8.5 & 10 Hz
B3
Conditions: CF₃SO₃CH₃/CH₂Cl₂/0°/1 hr.

Step C

Conditions: Pd(PPh₃)₄; PPh₃;

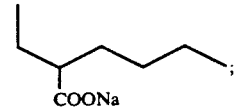

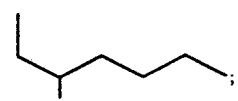

CH₂Cl₂: ether/0°/2 hr.
Yield: 57% of sulfide 50
UV: 305
ε: 4938
Yield: 31% of sulfoxide 53
UV: ~300
ε: 8167
Yield: 68% of sulfone 51
UV: ~300
ε: 7982
Yield: 26% of N-methylpyridinium sulfide 54
UV: 300
ε: 7553
Yield: 14% of N-methylpyridinium sulfoxide 56
UV: ~300
ε: 4725
Yield: 14% of N-methylpyridinium sulfone 57

UV: ~285
ε: 4867

EXAMPLES 55 AND 58

Step A

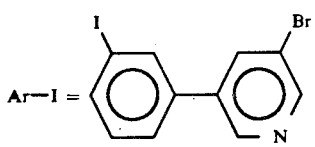

Conditions:
1) n-BuLi/ether/−78°/30 mins.
2) MgBr$_2$/THF
3) THF/0°/pyridylthioester Yield: 29% of ylide ketone

Step B

Step B1: Cyclization of the ylide ketone to carbapenem
Step B2: N-methylation of carbapenem pyridine
B1
Conditions: Xylene; 140°; 1 hr.
Yield: 67% of carbapenem
NMR:
H6: 3.42–3.46; dd; J=& 8.5 Hz
H5: 4.25–4.38; ddd; J=3; 8.5 & 10 Hz
B2
Conditions: CF$_3$SO$_3$CH$_3$; CH$_2$Cl$_2$; 0°; 1 hr. Crude product was used directly in deallylation

Step C:

Conditions: Pd (PPh$_3$)$_4$; PPh$_3$;

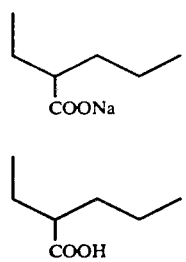

CH$_2$Cl$_2$: Ether; 2 hrs; 0°
Yield: 31% of 55 (bromopyridylphenyl)
UV: 303
ε: 3917
Yield: 25% of 58 (N-methylbromopyridiniumphenyl)
UV: ~300
ε: 2722
NMR: 4.74 (+N—CH$_3$; S)

EXAMPLE 61

Step A

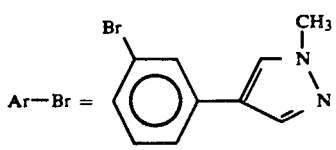

Conditions:

1) Grignard reagent preparation as in Kochetkov, S., *Doklady Nauk SSSR*, 133, 841–4 (1960)
2) Pyridylthioester; 30 min/0°; ambient temp/1 hr.
Yield: 26%
Spectra:
MS: m/e 262 (Ph$_3$P-base peak)
IR: (CH$_2$Cl$_2$): 1740 & 1680 (carbonyls); 1635 & 1610 (ylid) cm$^{-1}$.
$^1$H NMR: (300 MHz,CDCl$_3$): 1.17 (d, J=6 Hz, CH$_3$CHO—); 2.80 (br dd, H$_6$); 5.77–6.0 (m, CH=C) (selected absorbances).

Step B

Conditions: Xylene; 140° C.; 1.5 hr.
Yield: 64%
Spectra:
MS: m/e 477 (M+); 375 (M+—CH$_2$=CH—CH$_2$O$_2$COH).
IR: (CH$_2$Cl$_2$): 1780 (β-lactam); 1740 & 1715 (carbonates and ester).
$^1$H NMR: (300 MHz, CDCl$_3$): 1.49 (d, J=6 Hz, CH$_3$CHO—); 3.22 (dd, J=10 and 18 Hz, H$_{1a}$); 3.32 (dd, J=8 and 18 Hz, H$_{1b}$); 3.43 (dd, J=2 and 8 Hz, H$_6$); 3.94 (s, N—CH$_3$); 4.29 (dt, J=2 and 8 Hz, H$_5$); 4.58–4.73 (m, OCH$_2$C=C); 5.12–5.40 (m, C=CH$_2$); 5.76–6.00 (m, CH=C); 7.17–7.45 (m, aromatic protons); 7.59 & 7.73 (2 s's, pyrazole protons).

Step C

M=K
Conditions: Pd(PPh$_3$)$_4$; PPh$_3$

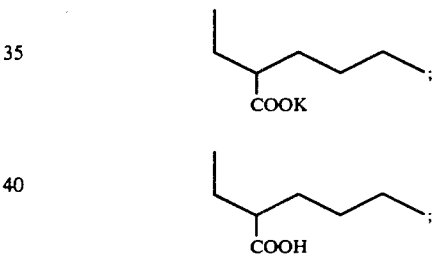

CH$_2$Cl$_2$: Ether; 0°; 2 hrs.
Yield: 43%
Spectra:
UV: (H$_2$O): λ$_{max}$=257 nm; λ (NH$_2$OH quenchable)=300 nm
ε: 11,000
$^1$H NMR: (200 MHz, D$_2$O): (no internal standard-DOH at 4.80); δ1.30 (d, J=6 Hz, CH$_3$CHO—); 3.07 (dd, J=10 and 18 Hz, H$_{1a}$); 3.43 (dd, J=8 and 18 Hz, H$_{1b}$); 3.52 (dd, J=3 and 6 Hz, H$_6$); 3.89 (s, N—Me); 4.23–4.36 (m, H$_5$ & H$_{1'}$); 7.20–7.52 (m, aromatic protons); 7.87 & 7.95 (2 s's, pyrazole protons).

EXAMPLE 62

Step A

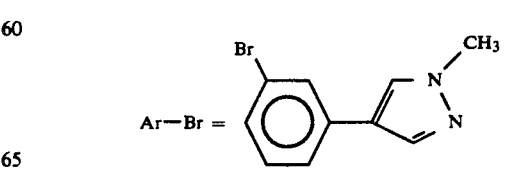

Conditions:
1) N-BuLi/−78°/THF

2) MgBr$_2$/THF
3) Pyridylthioester/THF; −78°/15 min; −20°/1 hr.
Yield: 9%
Spectra:
MS: m/e 671 (M$^+$—CO$_2$—CH$_2$CH=CH$_2$+H); 262 (Ph$_3$P).
IR: (CH$_2$Cl$_2$): 1740 (carbonyls); 1640 and 1615 (ylid) cm$^{-1}$.
$^1$H-NMR: (300 MHz, CDCl$_3$): 1.08 (d, J=6 Hz, CH$_3$CHO); 2.72 (dd, J=2 and 11 Hz, H$_6$); 5.67-5.94 (m, CH=C) (selected absorbances).

Step B

Conditions: Xylene; 140°; 1 hr
Yield: 78%
Spectra:
MS: m/e 477 (M$^+$); 307 ($\beta$-lactam cleavage.
IR: (CH$_2$Cl$_2$): 1780 ($\beta$-lactam); 1740 & 1715 (carbonates & ester) cm$^{-1}$. $^1$H NMR: (300 MHz, CDCl$_3$): 1.41 (d, J=6 Hz, CH$_3$CHO—); 3.17 (dd, J=10 and 18 Hz, H$_{1a}$); 3.26 (dd, J=9 and 18 Hz, H$_{1b}$), 3.33 (dd, J=3 and 9 Hz, H$_6$); 3.64 (s, NCH$_3$): 4.21 (dt, J=3 and 9 Hz, H$_5$); 4.49-4.66 (m, OCH$_2$C=C); 5.04-5.33 (m, CH=CH$_2$); 5.69-5.93 (m, —CH=C); 7.14-7.67 (m, aromatic protons), 7.38 & 7.69 (2 br. s's, imidazole protons).

Step C

M=K
Conditions: Pd(PPh$_3$)$_4$; PPh$_3$;

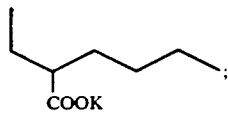

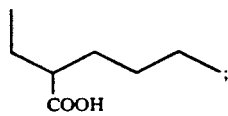

CH$_2$Cl$_2$:Ether; 2 hrs; 0°.
Yield: 64%
Spectra:
UV(H$_2$O): $\lambda_{max}$=266 nm; $\lambda$ (NH$_2$OH quenchable)=303 nm
$\epsilon$: 6,200
$^1$H NMR: (300 MHz, D$_2$O): (no internal standard-DOH at 4.80); 1.30 (d, J=6 Hz, CH$_3$CHO—); 3.08 (dd, J=10 and 18 Hz, H$_{1a}$); 3.45 (dd, J=8 and 18 Hz, H$_{1b}$); 3.52 (dd, J=3 and 8 Hz, H$_6$); 3.74 (s, N—CH$_3$); 4.21-4.33 (m, H$_5$ & H$_{1'}$); 7.26-7.62 (m, aromatic protons); 7.48 & 7.72 (2 br. s's, imidazole protons).

EXAMPLE 63

Step A

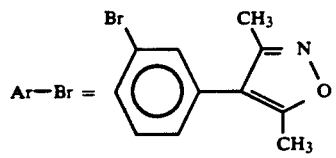

Conditions:

1) Kochetkov, S., *Doklady Nauk SSSR*, 133, 841-4 (1960)
2) Pyridylthioester/THF/0°/30 mins; ambient temp/1 hr.
Yield: ~50%

Step B

Conditions: Xylene; 140°; 1 hr.
Yield: 78%
Spectra:
$^1$H NMR: (300 MHz, CDCl$_3$): $\delta$1.49 (d, J=6 Hz; CH$_3$CHO—); 2.27 & 2.40 (2 s's, isoxazole methyls); 3.21 (dd, J=10 and 18 Hz, H$_{1a}$); 3.31 (dd, J=9 and 18 Hz, H$_{1b}$); 3.42 (dd, J=3 and 8 Hz, H$_6$); 4.27 (dt, J=3 and 10 Hz, H$_5$); 4.59-4.74 (m, —OCH$_2$C=C); 5.10-5.38 (m, C=CH$_2$ & H$_8$); 5.78-6.0 (m, CH=C); 7.20-7.45 (m, aromatic protons).

Step C

M=K
Conditions: Pd(PPh$_3$)$_4$; PPh$_3$;

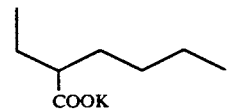

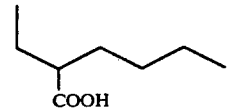

CH$_2$Cl$_2$: Ether; 0°; 2 hrs.
Yield: 41%
Spectra:
UV (H$_2$O): $\lambda_{max}$=266 nm; $\lambda$ (NH$_2$OH quenchable)=303 nm
$\epsilon$: 6,200
$^1$H NMR (300 MHz, D$_2$O): (no internal standard-DOH at 4.80); $\delta$1.25 (d, J=6 Hz, CH$_3$CHO); 2.18 & 2.34 (2 s's, isoxazole methyls); 3.02 (dd, J=10 and 17 Hz, H$_{1b}$); 3.45 (dd, J=3 and 6 Hz H$_6$); 4.15-4.28 (m, H$_5$ & H$_{1'}$); 7.22-7.44 (m, aromatic protons).

EXAMPLES 64, 65 and 66

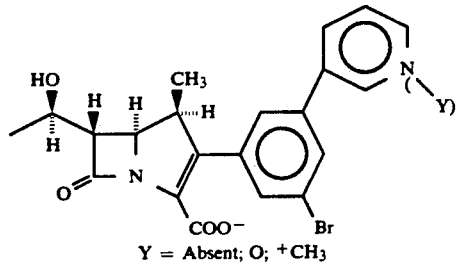

Y = Absent; O; $^+$CH$_3$

Step A

Conditions:
1)

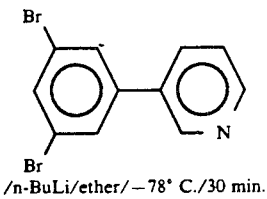

/n-BuLi/ether/−78° C./30 min.

2) MgBr$_2$/THF
3) β-Methylpyridylthioester; 0°; 15 min.
Yield: 39%
Spectra:
IR: 1740; 1683; 1620.

Step B

Step B1: cyclization of the ylide ketone to the carbapenem.
Step B2: N-methylation of pyridine of carbapenem.
Step B3: N-oxidation of pyridine of carbapenem.
B1
Conditions: Xylene; 140°; 19 hrs.
Yield: 93% of carbapenem.
Spectra:
IR: 1780; 1740; 1720.
NMR:
   CH$_3$'s; 1.14; d; J=8 Hz & 1.52; d;
   H6: 3.54–3.60; dd; J=3 & 8.5 Hz J=∼7 Hz;
   H5: 4.38–4.45; dd; J=3 & 10 Hz.
B2
Conditions: CF$_3$SO$_3$CH$_3$; CH$_2$Cl$_2$; 1 hr; 0° C. Crude product was used in deallylation.
B3
Conditions: mCPBA/NaHCO$_3$/1 hr/0°
Yield: ∼80%
Spectra:
IR: 1780; 1740; 1720.
NMR:
   CH$_3$'s; 1.12; d; J=8 Hz; 1.52; d; J=∼7 Hz;
   H6: 3.52–3.59; dd; J=3 & 8.5 Hz;
   H5: 4.38–4.44; dd; J=3 & 9 Hz.

Step C

Conditions: Pd(PPh$_3$)$_4$; PPh$_3$

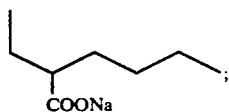

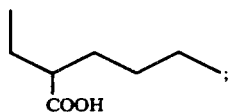

CH$_2$Cl$_2$: ether; 0°; 2 hrs.
Yield: ∼58% of 64
Spectra:
UV: ∼300
ε: 6324
Yield: ∼42% of 65
Spectra:
UV: ∼292
ε: 7312
Yield: ∼59% of 66
Spectra:
UV: ∼300
ε: 6638

What is claimed is:
1. A compound of the formula:

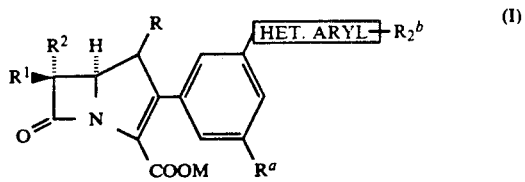

wherein:
R is H or CH$_3$;
R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

[HET. ARYL]

is (a) a monocyclic 5- or 6-membered aromatic ring system wherein at least one carbon atom is replaced by N, up to four additional carbon atoms may be replaced by N, and one carbon atom may be replaced by O or S; or (b) a bicyclic 9- or 10-membered aromatic ring system wherein at least one carbon atom is replaced by N, up to three additional carbon atoms may be replaced by N, and up to two carbon atoms may be replaced by S and/or O; with the proviso for both (a) and (b) that the atom in

[HET. ARYL]

at the point of attachment to the phenyl-R$^a$ ring is always carbon;

[HET. ARYL]

may be quaternized to form a cationic ring structure:

wherein R$_d$ is NH$_2$, O—, or C$_1$-C$_4$ alkyl (where the alkyl group is optionally monosubstituted with Rq as defined below); R$^a$ and R$^b$ are independently selected from the group consisting of hydrogen and the radicals set out below:
a) a trifluoromethyl group: —CF$_3$;
b) a halogen atom: —Br, —Cl, —F, or —I;
c) C$_1$-C$_4$ alkoxy radical: —OC$_1$-C$_4$ alkyl, wherein the alkyl is optionally mono-substituted by R$^q$, where
R$^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —SO$_3$M$^b$ (where M$^b$ is hydrogen or an alkali metal);

d) a hydroxy group: —OH;

e) a carbonyloxy radical: —O(C=O)R$^s$, where R$^s$ is C$_1$–$_4$ alkyl or phenyl, each of which is optionally mono-substituted by R$^q$ as defined above;

f) a carbamoyloxy radical: —O(C=O)N(R$^y$)R$^z$, where

R$^y$ and R$^z$ are independently H, C$_1$–C$_4$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)—, —S(O)$_2$— or —NR$^e$—, to form a ring (where R$^e$ is hydrogen, C$_1$–C$_4$ alkyl, and C$_1$–C$_4$ alkyl mono-substituted with R$^q$ and the ring is optionally mono-substituted with Rq as defined above);

g) a sulfur radical: —S(O)$_n$—R$^s$ where n=0-2, and R$^s$ is defined above;

h) a sulfamoyl group: —SO$_2$N(R$^y$)R$^z$ where R$^y$ and R$^z$ are as defined above;

i) azido: N$_3$ j) a formamido group: —N(R$^t$)—C(O)H, where R$^t$ is H or C$_1$–C$_4$ alkyl, and the alkyl thereof is optionally mono-substituted by R$^q$ as defined above;

k) a (C$_1$–C$_4$ alkyl) carbonylamino radical: —N(R$^t$)—C(O)C$_1$–C$_4$ alkyl, where R$^t$ is as defined above, and the alkyl group is also optionally mono-substituted by R$^q$ as defined above;

l) a (C$_1$–C$_4$ alkoxy) carbonylamino radical: —N(R$^t$)—C(O)OC$_1$–$_4$ alkyl, where R$^t$ is as defined above, and the alkyl group is also optionally mono-substituted by R$^q$ as defined above;

m) a ureido group: —N(R$^t$)—C(O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —C(O)H or —C(OCH$_3$)$_2$H;

q) (C$_1$–C$_4$ alkyl) carbonyl radical wherein the carbonyl is acetalized: —C(OCH$_3$)$_2$C$_1$–$_4$ alkyl, where the alkyl is optionally mono-substituted by R$^q$ as defined above;

r) carbonyl radical: —C(O)R$^s$, where R$^s$ is as defined above;

s) a hydroximinomethyl radical in which the oxygen or carbon atom is optionally substituted by a C$_1$–C$_4$ alkyl group: —C(R$^y$)=NOR$^z$ where R$^y$ and R$^z$ are as defined above, except they may not be joined together to form a ring;

t) a (C$_1$–C$_4$ alkoxy) carbonyl radical: —C(O)OC$_1$–C$_4$ alkyl, where the alkyl is optionally mono-substituted by R$^q$ as defined above;

u) a carbamoyl radical: —C(O)N(R$^y$)R$^z$ where R$^y$ and R$^z$ are as defined above;

v) an N-hydroxycarbamoyl or N(C$_1$–C$_4$ alkoxy) carbamoyl radical in which the nitrogen atom may be additionally substituted by a C$_1$–C$_4$ alkyl group: —(C=O)—N(OR$^y$)R$^z$ where R$^y$ and R$^z$ are as defined above, except they may not be joined together to form a ring;

w) a thiocarbamoyl group: —C(S)N(R$^y$)(R$^z$) where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a C$_1$–C$_4$ alkyl optionally substituted by R$^q$ as defined above;

ab) an anionic function selected from the group consisting of: phosphono [P=O(OM$^b$)$_2$]; alkylphosphono {P=O(OM$^b$)—[O(C$_1$–C$_4$ alkyl)]}; alkylphosphinyl [P=O(OM$^b$)—(C$_1$–C$_4$ alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_2$–C$_4$ alkenyl radical, optionally mono-substituted by one of the substituents a) to ab) above and phenyl which is optionally substituted by R$^q$ as defined above;

ad) C$_2$–C$_4$ alkynyl radical, optionally mono-substituted by one of the substituents a) to ab) above;

ae) C$_1$–C$_4$ alkyl radical;

af) C$_1$–C$_4$ alkyl mono-substituted by one of the substituents a)–ab) above;

ag) an amino group, NR$^t_2$, wherein R$^t$ is as defined above;

M is selected from:
  i) hydrogen;
  ii) a pharmaceutically acceptable esterifying group or removable carboxyl protecting group;
  iii) an alkali metal or other pharmaceutically acceptable cation; or
  iv) a negative charge which is balanced by a positively charged group.

2. A compound of claim 1 wherein R$^1$ is hydrogen.

3. A compound of claim 1 wherein R$^1$ is hydrogen and R$^2$ is (R)—CH$_3$CH(OH)— or (R)—CH$_3$CH(F)—.

4. A compound of claim 3 wherein R$^a$ is C$_1$–C$_4$ alkyl mono-substituted with hydroxy, formyl, carboxy, carbamoyl, hydroxyiminomethyl, cyano, or halogen.

5. A compound of claim 3 wherein R$^b$ is independently:

| | |
|---|---|
| —OCH$_3$ | |
| —OCH$_2$CH$_2$OH | —OCH$_2$CO$_2$Na |
| —F | —CF$_3$ |
| —Br | —Cl |
| —OH | —I |
| —OCONH$_2$ | —OCOCH$_3$ |
| —SOCH$_3$ | —SCH$_3$ |
| —SCH$_2$CH$_2$OH | —SO$_2$CH$_3$ |
| —SO$_2$NH$_2$ | —SOCH$_2$CH$_2$OH |
| —NHCHO | —SO$_2$N(CH$_3$)$_2$ |
| —NHCO$_2$CH$_3$ | —NHCOCH$_3$ |

| -continued | |
|---|---|
| —CN | —NHSO$_2$CH$_3$ |
| —COCH$_3$ | —CHO |
| —CH=NOH | —COCH$_2$OH |
| —CH=NOCH$_2$CO$_2$H | —CH=NOCH$_3$ |
| —SO$_2$CH$_2$CH$_2$OH | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na and | —CH$_2$I |

6. A compound of claim 1 of the formula

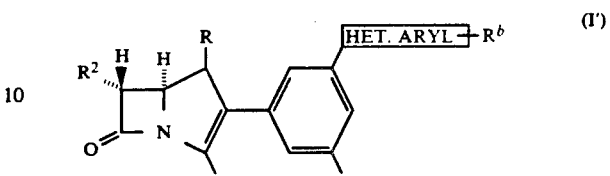   (I')

where R$^2$ containing a chiral center is in the (R) configuration;
wherein the substituents are as follows:

| No. | R | R$^2$ | M | R$^a$ | HET. ARYL—R$^b$ |
|---|---|---|---|---|---|
| 1 | H | —CH(OH)CH$_3$ | Na | H | 3-pyridyl |
| 2 | H | —CH(OH)CH$_3$ | Na | Cl | 3-pyridyl |
| 3 | H | —CH(OH)CH$_3$ | Na | Br | 3-pyridyl |
| 4 | H | —CH(OH)CH$_3$ | Na | I | 3-pyridyl |
| 5 | H | —CH(OH)CH$_3$ | Na | SMe | 3-pyridyl |
| 5a | H | —CH(OH)CH$_3$ | (—) | SMe | N-methyl-3-pyridinium |
| 6 | H | —CH(OH)CH$_3$ | Na | S(O)Me | 3-pyridyl |
| 7 | H | —CH(OH)CH$_3$ | Na | SO$_2$Me | 3-pyridyl |
| 8 | H | —CH(OH)CH$_3$ | Na | F | 3-pyridyl |

-continued

| No. | R | R² | M | Rᵃ | HET. ARYL—Rᵇ |
|---|---|---|---|---|---|
| 9 | H | —CH(OH)CH₃ | (—) | H | 3-methyl-N-methylpyridinium |
| 10 | H | —CH(OH)CH₃ | Na | H | 3-methylpyridine N-oxide |
| 11 | H | —CH(OH)CH₃ | (—) | F | 3-methyl-N-methylpyridinium |
| 12 | H | —CH(OH)CH₃ | Na | F | 3-methylpyridine N-oxide |
| 13 | H | —CH(OH)CH₃ | (—) | Br | 3-methyl-N-methylpyridinium |
| 14 | H | —CH(OH)CH₃ | Na | Br | 3-methylpyridine N-oxide |
| 15 | H | —CH(OH)CH₃ | (—) | I | 3-methyl-N-methylpyridinium |
| 16 | H | —CH(OH)CH₃ | Na | I | 3-methylpyridine N-oxide |
| 17 | H | —CH(OH)CH₃ | (—) | Cl | 3-methyl-N-methylpyridinium |

-continued

| No. | R | R² | M | Rᵃ | HET. ARYL—Rᵇ |
|---|---|---|---|---|---|
| 18 | H | —CH(OH)CH₃ | Na | Cl | 3-pyridyl N-oxide |
| 19 | H | —CH(OH)CH₃ | Na | H | 3-quinolinyl |
| 20 | H | —CH(OH)CH₃ | (—) | H | 3-(1-methylquinolinium) |
| 21 | H | —CH(OH)CH₃ | Na | H | 3-isoquinolinyl |
| 22 | H | —CH(OH)CH₃ | (—) | H | 3-(2-methylisoquinolinium) |
| 23 | H | —CH(OH)CH₃ | Na | H | 6-quinolinyl |
| 24 | H | —CH(OH)CH₃ | (—) | H | 6-(1-methylquinolinium) |
| 25 | H | —CH(OH)CH₃ | Na | H | 6-isoquinolinyl |
| 26 | H | —CH(OH)CH₃ | (—) | H | 6-(2-methylisoquinolinium) |
| 27 | H | —CH(OH)CH₃ | Na | I | 3-quinolinyl |
| 28 | H | —CH(OH)CH₃ | (—) | I | 3-(1-methylquinolinium) |

-continued
| No. | R | R² | M | Rᵃ | HET. ARYL—Rᵇ |
|---|---|---|---|---|---|
| 29 | H | —CH(OH)CH₃ | Na | I | 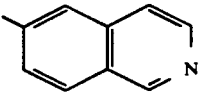 |
| 30 | H | —CH(OH)CH₃ | (—) | I | 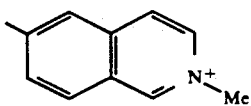 |
| 31 | H | —CH(OH)CH₃ | Na | H | 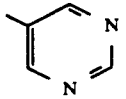 |
| 32 | H | —CH(OH)CH₃ | Na | I | 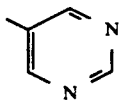 |
| 33 | H | —CH(OH)CH₃ | Na | H | 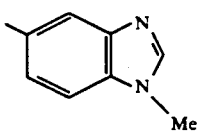 |
| 34 | H | —CH(OH)CH₃ | Na | CN | 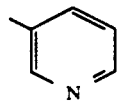 |
| 35 | H | —CH(OH)CH₃ | Na | H | 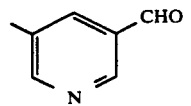 |
| 36 | H | —CH(OH)CH₃ | Na | I | 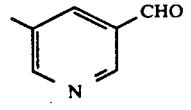 |
| 37 | H | —CH(OH)CH₃ | Na | H | 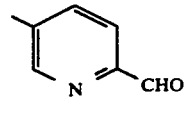 |
| 38 | H | —CH(OH)CH₃ | Na | I | 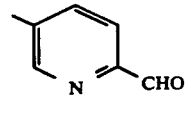 |
| 39 | H | —CH(OH)CH₃ | (—) | I | 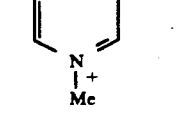 |
| 40 | H | —CH(OH)CH₃ | Na | H | 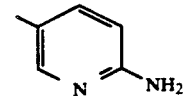 |

-continued

| No. | R | R² | M | Rᵃ | HET. ARYL—Rᵇ |
|---|---|---|---|---|---|
| 41 | H | —CH(OH)CH₃ | (—) | H | 2-amino-5-methyl-1-methylpyridinium |
| 42 | H | —CH(OH)CH₃ | (—) | I | 2-amino-5-methyl-1-methylpyridinium |
| 43 | CH₃ | —CH(OH)CH₃ | Na | Br | 5-methylpyridin-3-yl |
| 44 | CH₃ | —CH(OH)CH₃ | (—) | Br | 5-methyl-1-methylpyridinium-3-yl |
| 45 | CH₃ | —CH(OH)CH₃ | (—) | Br | 5-methylpyridine N-oxide |
| 46 | CH₃ | —CH(OH)CH₃ | Na | I | 5-methylpyridin-3-yl |
| 47 | CH₃ | —CH(OH)CH₃ | (—) | I | 5-methyl-1-methylpyridinium-3-yl |
| 48 | H | —CH(F)CH₃ | (—) | I | 5-methyl-1-methylpyridinium-3-yl |
| 49 | H | —CH(F)CH₃ | Na | I | 5-methylpyridin-3-yl |
| 50 | H | —CH(F)CH₃ | Na | I | 5-methyl-3-formylpyridine |
| 51 | H | —CH(OH)CH₃ | Na | H | 5-methyl-3-(methylsulfonyl)pyridine |

-continued
| No. | R | R² - | M | Rᵃ | HET. ARYL—Rᵇ |
|---|---|---|---|---|---|
| 52 | H | —CH(OH)CH₃ | Na | H | 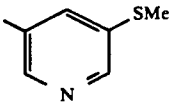 |
| 53 | H | —CH(OH)CH₃ | Na | H | 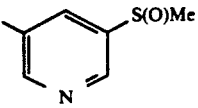 |
| 54 | H | —CH(OH)CH₃ | (—) | H | 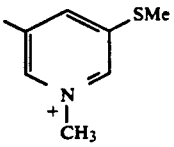 |
| 55 | H | —CH(OH)CH₃ | (—) | H | 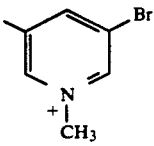 |
| 56 | H | —CH(OH)CH₃ | (—) | H | 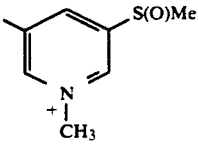 |
| 57 | H | —CH(OH)CH₃ | (—) | H | 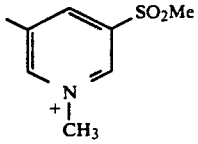 |
| 58 | H | —CH(OH)CH₃ | Na | H | 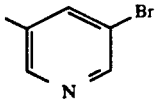 |
| 59 | H | —CH(OH)CH₃ | Na | SO₂Me | 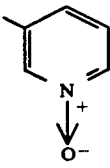 |
| 60 | H | —CH(OH)CH₃ | (—) | I | 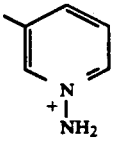 |
| 61 | H | —CH(OH)CH₃ | K | H | 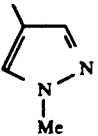 |

| No. | R | $R^2$ | M | $R^a$ | HET. ARYL—$R^b$ |
|---|---|---|---|---|---|
| 62 | H | —CH(OH)CH₃ | K | H | 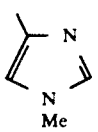 |
| 63 | H | —CH(OH)CH₃ | K | H | 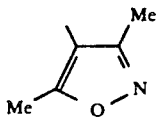 |
| 64 | CH₃ | —CH(OH)CH₃ | Na | Br | 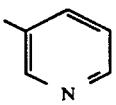 |
| 65 | CH₃ | —CH(OH)CH₃ | (—) | Br | 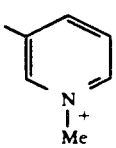 |
| 66 | CH₃ | —CH(OH)CH₃ | Na | Br | 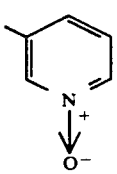 |

7. A pharmaceutical composition effective against bacteria comprising an effective amount of a compound of claim 1 and a pharmaceutically acceptable carrier therefor.

8. A method for treating baterial infection in mammals comprising administering a pharmaceutical composition comprising an effective amount of a compound of claim 1 and a pharmaceutically acceptable carrier therefor.

9. A composition according to claim 7 which further comprises an inhibitorily effective amount of a DHP inhibitor.

10. A composition according to claim 9 wherein said DHP inhibitor is 7-(L-2-amino-2-carboxyethylthio)-2-(2,2-dimethylcyclopropanecarboxamide)-2-heptanoic acid.

11. A method according to claim 8 which further comprises administering an inhibitorily effective amount of a DHP inhibitor.

12. A method according to claim 11 wherein said DHP inhibitor is 7-(L-2-amino-2-carboxyethylthio)-2-(2,2-dimethylcyclopropanecarboxamide)-2-heptanoic acid.

* * * * *